United States Patent
Richomme et al.

(10) Patent No.: US 10,494,357 B2
(45) Date of Patent: Dec. 3, 2019

(54) TOCOTRIENOL DERIVATIVES, PHARMACEUTICAL COMPOSITION AND METHOD OF USE IN 5-LIPOXYGENASE RELATED DISEASES

(71) Applicants: UNIVERSITÉ D'ANGERS, Angers (FR); UNIVERSITÄT INNSBRUCK, Innsbruck (AT); FRIEDRICH-SCHILLER-UNIVERSITÄT JENA, Jena (DE)

(72) Inventors: Pascal Richomme, Angers (FR); Jean-Jacques Helesbeux, Soulaines sur Aubance (FR); David Guilet, Angers (FR); Denis Seraphin, Saint Saturnin sur Loire (FR); Hermann Stuppner, Götzens (AT); Birgit Waltenberger, Innsbruck (AT); Daniela Schuster, Telfs (AT); Veronika Sophie Temml, Innsbruck (AT); Andreas Koeberle, Sigmaringendorf (DE); Oliver Werz, Jena (DE)

(73) Assignees: UNIVERSITÉ D'ANGERS, Angers (FR); UNIVERSITÄT INNSBRUCK, Innsbruck (AT); FRIEDRICH-SCHILLER-UNIVERSITÄT JENA, Jena (DE)

( * ) Notice: Subject to any disclaimer, the term of this patent is extended or adjusted under 35 U.S.C. 154(b) by 0 days.

(21) Appl. No.: 15/755,244

(22) PCT Filed: Aug. 26, 2016

(86) PCT No.: PCT/EP2016/070204
§ 371 (c)(1),
(2) Date: Feb. 26, 2018

(87) PCT Pub. No.: WO2017/032881
PCT Pub. Date: Mar. 2, 2017

(65) Prior Publication Data
US 2019/0144413 A1   May 16, 2019

(30) Foreign Application Priority Data
Aug. 27, 2015   (EP) ..................... 15182827

(51) Int. Cl.
C07D 311/72 (2006.01)
A61P 11/06 (2006.01)

(52) U.S. Cl.
CPC ............ *C07D 311/72* (2013.01); *A61P 11/06* (2018.01)

(58) Field of Classification Search
None
See application file for complete search history.

(56) References Cited

U.S. PATENT DOCUMENTS

2006/0193797 A1   8/2006   Zhang et al.
2015/0073044 A1   3/2015   Jiang

FOREIGN PATENT DOCUMENTS

WO   2006/135368   12/2006
WO   2010/033687   3/2010

OTHER PUBLICATIONS

Lavaud, A. et al., Phytochemistry 2015, vol. 109, 103-110.*
Maloney, D. et al Org. Lett. 2005 vol. 7 pp. 4297-4300.*
Alexis Lavaud et al: "Antiangiogenic tocotrienol derivatives from Garcinia amplexicaulis", Journal of Natural Products, American Chemical Society, US, vol. 76, No. 12, Dec. 27, 2013 (Dec. 27, 2013), pp. 2246-2252, XP002747230, ISSN: 0163-3864, DOI: 10.1021/NP400598Y [retrieved on Nov. 18, 2013] the whole document.
Pallu Reddanna et al: "Inhibition of 5-lipoxygenase by vitamin E"., Center for Air Environment Studies and Department of Veterinary Science, The Pennsylvania State University, University Park. PA 16802, USA, vol. 193, No. 1, Received Oct. 9, 1985, pp. 39-43.

* cited by examiner

*Primary Examiner* — Heidi Reese
(74) *Attorney, Agent, or Firm* — Young & Thompson

(57) ABSTRACT

The present invention relates to compounds of formula (III)

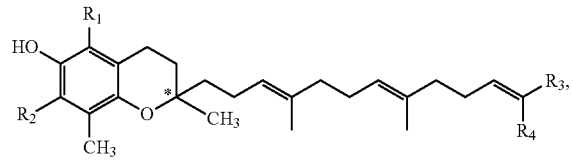

or to compounds of formula (IV)

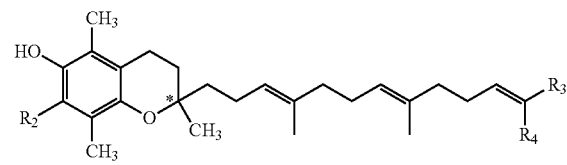

wherein $R_1$, $R_2$, $R_3$ and $R_4$ are as defined in the claims, and their use in therapeutic treatments of 5-lipoxygenase related diseases such as chronic airway inflammatory or dermatological disorders.

11 Claims, 3 Drawing Sheets

TOCOTRIENOL DERIVATIVES, PHARMACEUTICAL COMPOSITION AND METHOD OF USE IN 5-LIPOXYGENASE RELATED DISEASES

FIELD OF INVENTION

The present invention relates to novel tocotrienol derivatives including their pharmaceutically acceptable solvates that both inhibit human semi-purified 5-lipoxygenase (5-LO) activity and 5-LO product formation in intact human neutrophils. These tocotrienol derivatives are useful as therapeutic compounds, particularly in the treatment and/or prevention of 5-LO related diseases, among which dermatological diseases, respiratory track diseases and chronic airway inflammatory diseases such as asthma.

BACKGROUND OF INVENTION

Lipoxygenases are a family of iron-containing enzymes that act as catalysts of the oxidation reaction of polyunsaturated fatty acids or other alkenes. Among them, the 5-lipoxygenase (also called 5-LO) catalyzes the oxygenation of arachidonic acid (AA) for providing leukotrienes which are a group of lipid inflammation mediators. Consequently, 5-LO is involved in various diseases, especially, in inflammatory diseases.

Asthma is a chronic inflammatory disorder of the airways in which many cells and cellular elements play a role. This chronic inflammation causes an increase in airway hyperresponsiveness due to certain factors such as allergens, tobacco smoke, chemicals, pollution or some strong emotions.

According to the World Health Organization, asthma affects 235 million people and is characterized by recurrent episodes of wheezing, breathlessness chest tightness and coughing, particularly at night or in the early morning. These episodes are usually associated with widespread but variable airflow obstruction that is often reversible either spontaneous or with the treatment. The severity and frequency of such recurrent episodes may vary from one person to another. However, an appropriate management of the disease can control the troubles and enable to ensure a good quality of life to patients.

To date, different types of treatment are available depending on the degree of severity of the disease in the patient and whether it is a treatment to relieve (in the case of a crisis) or to prevent (background treatment). These treatments are mainly based on decreasing local hyper reactivity of bronchi and/or inflammation.

Biochemical markers of inflammation are known in the art. The presence of elevated levels of these markers has been shown to be associated with the development of inflammatory diseases.

In the case of asthma, the crucial involvement of 5-lipoxygenase (or 5-LO) in mediating disease symptoms is known. The 5-LO catalyzes the conversion of arachidonic acid (AA) into leukotrienes $A_4$ ($LTA_4$) (See FIG. 1). Then, depending on the cell type and the enzymes present, unstable $LTA_4$ can be converted either into leukotriene $B_4$ ($LTB_4$) or into leukotriene comprising a cysteine moiety (CysLT): $LTC_4$, $LTD_4$ and $LTE_4$. CysLT play a prominent role in asthma. Indeed, they were identified as potent mediators of bronchoconstriction and hypersensitivity reactions. $LTB_4$ is a chemotactic agent and promotes inflammation.

To date, few therapeutic agents have been authorized by the FDA or other health authorities as efficient anti-asthmatic drugs; especially by acting through the 5-LO mechanism as described above.

Montelukast (SINGULAIR®) and zafirlukast (ACCOLATE®) are both leukotriene receptor antagonists which inhibit the activity of specific leukotrienes. However, they do not allow acting on the 5-LO and in particular, they do not allow inhibiting leukotriene synthesis.

Zileuton (ZYFLO®) is an orally active inhibitor of 5-LO (both on activity and on 5-LO product formation) acting by an iron-chelating mechanism.

Scheme 1. Structure of Zileuton.

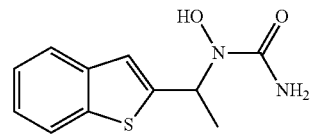

Due to its unfavorable pharmacokinetics (short half-life time), Zileuton-based treatment requires the intake of 600 mg four times a day. This elevated daily amount of drug induces 1) significant side effects such as hepatic issues and neuropsychiatric disorders and 2) contributes to the expensiveness of the treatment.

Thus, in view of the disadvantages as described above, there is a need for providing new treatments for asthma to overcome the drawbacks described above. Especially, there is a need for providing cheaper treatment while enhancing bioavailability for the comfort of the patient without side effects.

There is also a need to provide new compounds allowing the efficient inhibition of 5-LO and subsequently of the production of leukotrienes.

WO2006/093547 (Zhang et al.) reports the inhibition of lipoxygenases by chromanol compounds and their use as therapeutic agents for the treatment of apoptosis of cancer cells.

WO2005/013911 (Sen et al.) reports a method for inhibiting the 12-lipoxygenase in a patient in need thereof, comprising the administration of an efficient amount of tocotrienols.

Reddanna et al. ("Inhibition of 5-lipoxygenase by vitamin E", *FEBS Letters*, Vol. 193, N° 1, November 1985, pages 39-43) reports the irreversible and non-competitive inhibition of the 5-LO by vitamin E composed of a set of 8 molecules: 4 tocopherols (α, β, γ, δ) and 4 tocotrienols (α, β, γ, δ), whose structures are presented as below:

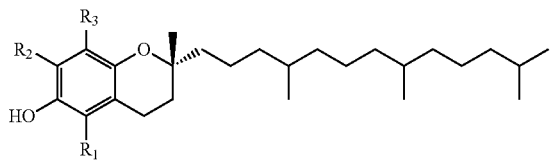

Tocopherol

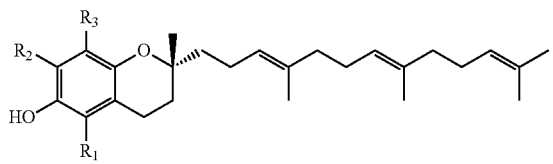

Tocotrienol

| Compound | R1 | R2 | R3 |
|---|---|---|---|
| Alpha (α) | CH₃ | CH₃ | CH₃ |
| Beta (β) | CH₃ | H | CH₃ |
| Gamma (γ) | H | CH₃ | CH₃ |
| Delta (δ) | H | H | CH₃ |

WO00/72862 (Nawar et al.) reports an oil extract of cranberry comprising tocopherols and tocotrienols and suggests its use for the treatment or prevention of conditions associated with the activity of 5-LO.

WO2010/033687 (Gibbs et al.) reports long-chain carboxychromanol compounds comprising a carboxy group at its terminal as useful for treating conditions associated with the need to inhibit the activity of cyclooxygenases or lipoxygenases.

To the Applicant's knowledge, the closest prior art, disclosing δ-garcinoic acid for 5-LO, is US2015/0073044. However, δ-garcinoic acid is not efficient enough to achieve therapeutical purposes; especially, in dermatological and/or chronic airways diseases.

The goal of this invention is providing new compounds allowing inhibiting neutrophil 5-LO product formation (leukotriene formation) in addition to the inhibition of the activity of the 5-LO. None of prior art documents provide compounds allowing inhibition of neutrophil 5-LO product formation (leukotriene formation) with an efficient bioavailability in the organism of the patient treated for 5-LO related diseases. Especially, none of the cited prior art provides therapeutic compounds allowing achievement of efficient plasmatic concentration in a patient treated for chronic airways disorders and/or dermatological diseases.

Surprisingly, the Applicant has highlighted that tocotrienol derivatives inhibit the 5-lipoxygenase via another binding site than that of the natural substrate, the arachidonic acid. This new way provides reversible and noncompetitive inhibitors of both the 5-LO activity and of 5-LO product formation, allowing reducing side effects of treatment.

SUMMARY

This invention thus relates to a tocotrienol derivative of general formula (IV)

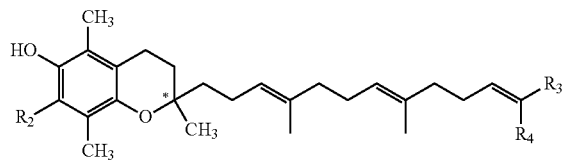

and pharmaceutically acceptable salts and/or solvates thereof, wherein:
* stands for the (R)-enantiomer, the (S)-enantiomer, for the racemate or for the non racemic mixture of (R) and (S) enantiomers of the corresponding formula (IV);

$R_2$ is H or alkyl; preferably, $R_2$ is H or C1-C6 alkyl; more preferably $R_2$ is H or $CH_3$;

$R_3$ and $R_4$ are identical or different and each one is selected from the group of amido, alkyl, carboxyl, hydroxyl and formyl; wherein alkyl is optionally substituted by at least one group selected from hydroxyl, carboxyl, oxo, amido, amino and formyl; wherein amido group is optionally substituted by at least one group selected from alkyl, arylalkyl or alkylaryl; preferably $R_3$ and $R_4$ are identical and represent $CH_2OH$; preferably $R_3$ is $CH_3$ and $R_4$ is carboxyl; preferably $R_3$ is carboxyl and $R_4$ is $CH_3$; and wherein at least one of $R_3$ or $R_4$ is an alkyl substituted by at least one group selected from hydroxyl, carboxyl or formyl.

According to one embodiment, the tocotrienol derivative of formula (IV) is the (R)-enantiomer.

In one embodiment, preferred compounds of formula (IV) are compounds wherein $R_2$ is $CH_3$.

In one embodiment, preferred compounds of formula (IV) are compounds wherein $R_3$ and $R_4$ are selected such that the stereochemistry of double bond C=C to which they are attached is (E).

In one embodiment, preferred compound of formula (IV) is selected from:

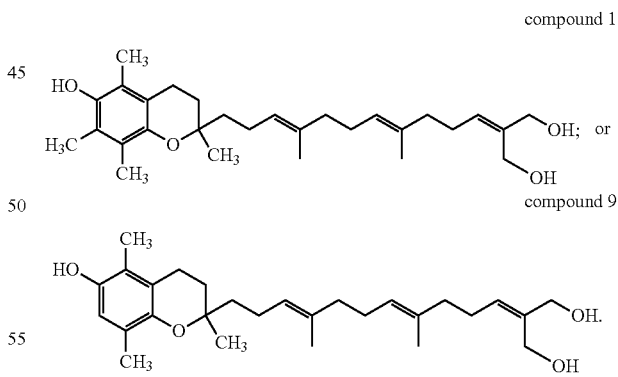

The present invention also relates to a pharmaceutical composition comprising at least one tocotrienol derivative of formula (IV), and at least one pharmaceutically acceptable carrier, diluent, excipient and/or adjuvant.

The present invention also relates to a medicament comprising at least one tocotrienol derivative of formula (IV), or pharmaceutically acceptable salts and/or solvates thereof.

The present invention also relates to a tocotrienol derivative of general formula (III)

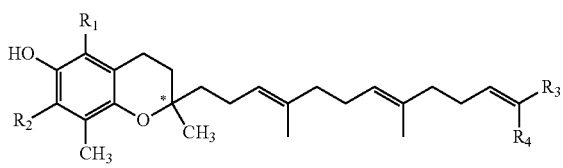

and pharmaceutically acceptable salts and/or solvates thereof, wherein:
* stands for the (R)-enantiomer, the (S)-enantiomer, for the racemate or for the non-racemic mixture of (R) and (S) enantiomers of the corresponding formula (III);
$R_1$ is H or alkyl; preferably $R_1$ is H or C1-C6 alkyl; more preferably, $R_1$ is $CH_3$;
$R_2$ is H or alkyl; preferably, $R_2$ is H or C1-C6 alkyl; more preferably, $R_2$ is H or $CH_3$;
$R_3$ and $R_4$ are identical or different and each one is selected from the group of amido, alkyl, carboxyl, hydroxyl and formyl; wherein alkyl is optionally substituted by at least one group selected from hydroxyl, carboxyl, oxo, amido, amino and formyl; wherein amido group is optionally substituted by at least one group selected from alkyl, arylalkyl or alkylaryl; preferably $R_3$ and $R_4$ are identical and represent $CH_2OH$; preferably $R_3$ is $CH_3$ and $R_4$ is carboxyl; preferably $R_3$ is carboxyl and $R_4$ is $CH_3$; and
wherein at least one of $R_3$ or $R_4$ is an alkyl substituted by at least one group selected from hydroxyl, carboxyl or formyl;
for use in the treatment of a 5-LO mediated disease;
provided that compound of formula (III) is not 6-garcinoic acid.

In one embodiment, the 5-LO mediated disease is selected from chronic airways disorders and/or dermatological diseases.

In one embodiment, the 5-LO mediated disease is asthma.

In one embodiment, the 5-LO mediated disease is selected from dermatological diseases, preferably, the 5-LO mediated disease is atopic dermatitis.

In one embodiment, preferred compounds of formula (III) are those wherein the tocotrienol derivative inhibits the 5-LO activity.

In one embodiment, preferred compounds of formula (III) are those wherein the tocotrienol derivative inhibits the neutrophil 5-LO product formation.

In one embodiment, preferred compounds of formula (III) are those wherein the tocotrienol derivative inhibits both the 5-LO activity and the neutrophil 5-LO product formation.

DEFINITIONS

The definitions and explanations below are for the terms as used throughout the entire application, including both the specification and the claims.

When describing the compounds of the invention, the terms used are to be construed in accordance with the following definitions, unless indicated otherwise.

The term "alkyl" refers to a hydrocarbyl radical of formula $C_nH_{2n+1}$ wherein n is a number greater than or equal to 1. Generally, alkyl groups of this invention comprise from 1 to 6 carbon atoms, preferably from 1 to 3 carbon atoms. Alkyl groups may be linear or branched. Suitable alkyl groups include but are not limited to methyl, ethyl, n-propyl, i-propyl, n-butyl, i-butyl, s-butyl; t-butyl, n-pentyl, i-pentyl, s-pentyl and t-pentyl; n-hexyl, i-hexyl, s-hexyl and t-hexyl.

The term "heteroalkyl" refers to any alkyl group comprising at least one heteroatom, preferably selected from O, N, S or P.

The term "heterocycloalkyl" refers to any cycloalkyl group comprising at least one heteroatom, preferably selected from O, N, S or P.

The term "alkoxyl" refers to any O-alkyl or O-aryl group.

The term "amido" refers to —NR—CO— wherein R represents either an atom H or an alkyl group as defined above.

The term "amino" refers to a —$NH_2$ group or any group derived thereof by substitution of one or two hydrogen atom by an organic aliphatic or aromatic group. Preferably, groups derived from —$NH_2$ are alkylamino groups, such as N-alkyl groups, comprising monoalkylamino and dialkylamino.

The term "carboxyl" refers to —COOH.

The term "oxo" refers to —C=O function.

The term "cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms, and even more preferably from 3 to 6 carbon atoms. Examples of cycloalkyl groups include but are not limited to cyclopentyl or cyclohexyl.

The term "ester" refers to any —COO— group.

The term "formyl" refers to a —CHO.

The term "hydroxyl" refers to —OH.

The term "aryl" as used herein refers to a polyunsaturated, aromatic hydrocarbyl group having a single ring eventually comprising an heteroatom (such as phenyl, dioxan, pyridine, piperidin, morpholin, piperazin or pyrrole) or multiple aromatic rings fused together (e.g. naphtyl). or linked covalently, typically containing 5 to 12 atoms; preferably 6 to 10, wherein at least one ring is aromatic. The aromatic ring may optionally include one or two additional rings (cycloalkyl, heterocyclyl or heteroaryl) fused thereto. The aryl ring can optionally be substituted by one or more substituent(s).

The chromanol core in compounds of the invention is numbered based on the scheme below.

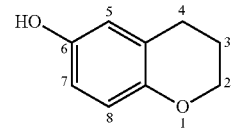

Bonds from an asymmetric carbon in compounds are generally depicted using a solid line (——), a solid wedge (▬) or a dotted wedge (⋯).The use of either a solid or a dotted wedge to depict bonds from an asymmetric carbon atom is meant to indicate that only the stereoisomer shown is meant to be included.

The compounds of formula (I) and subformulae thereof contain a stereogenic carbon center at position 2 and thus may exist as (R)- and (S)-enantiomers.

The term "neutrophil" refers to a type of granulocytes of white blood cells in mammals and are first-responders of inflammatory cells. Especially, in the present invention, "neutrophils" refers to leukotrienes resulting from the activity of the 5-lipoxygenase.

The term "solvate" is used herein to describe a compound in this invention that contains stoichiometric or sub-stoichiometric amounts of one or more pharmaceutically acceptable solvent molecules. The term "hydrate" refers to water solvent.

All references to compounds of formula (I) include references to solvates, multi-component complexes and liquid crystals thereof.

The compounds of the invention include compounds of formula (I) as hereinbefore defined, including all polymorphs and crystal habits thereof, predrugs and prodrugs thereof and isotopically-labeled compounds of formula (I).

The invention also generally covers all pharmaceutically acceptable predrugs and prodrugs of the compounds of formula (I).

The term "prodrug" as used herein means the pharmacologically acceptable derivatives of compounds of formula (I), such as for example esters or amides, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting the receipt of, or is receiving medical care or is/will be the object of a medical procedure.

The term "human" refers to a subject of both genders and at any stage of development (such as neonate, infant, juvenile, adolescent, adult).

The terms "treat", "treating" and "treatment", as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e.g. 5-LO inhibitor and/or 5-LO product formation inhibitor) that is sufficient to achieve the desired therapeutic or prophylactic effect in the patient to which/whom it is administered.

The term "administration", or a variant thereof (e.g. "administering"), means providing the active agent or active ingredient (e.g. 5-LO inhibitor and/or 5-LO product formation inhibitor), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "5-LO mediated disease" as used herein means a disease or a condition which is exacerbated by, or caused by, excessive, inappropriate or unregulated 5-lipoxygenase (5-LO) activity or production. The term "5-LO mediated disease" includes all medical conditions alleviated by treatment with a 5-LO agonist and includes all disease states and/or conditions that are acknowledged now, or that will be found in the future, to be associated with 5-LO activity. Examples of such diseases in a subject include but not limited to, chronic airway inflammatory diseases such as asthma, chronic obstructive pulmonary disease (COPD), aspirin-induced asthma, allergic rhinitis, sinusitis, chronic bronchitis or anaphylaxis; or inflammatory skin diseases such as atopic dermatitis. The term "chronic airway inflammatory diseases" also includes all respiratory system diseases.

DETAILED DESCRIPTION

Tocotrienol Derivatives

As noted above, the invention relates to a tocotrienol derivative of formula (I):

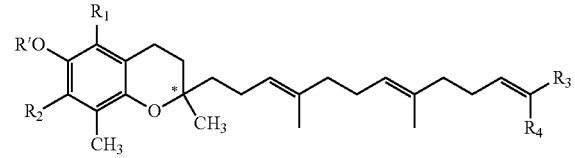

and pharmaceutically acceptable salts and/or solvates thereof, wherein:

* stands for the (R)-enantiomer, the (S)-enantiomer, for the racemate or for the non racemic mixture of (R) and (S) enantiomers of the corresponding formula (I);

$R_1$ is H, formyl, amino, alkylamino or alkyl; wherein alkyl is optionally substituted by at least one group selected from hydroxyl, amino, alkylamino, aryl, heteroaryl, alkylaryl, alkylheteroaryl, cycloalkyl, heterocycloalkyl, alkylcycloalkyl or alkylheterocycloalkyl; preferably $R_1$ is H, formyl, $CH_3$, alkylpiperazinylalkyl, morpholinoalkyl, alkylmorpholinoalkyl, alkylpiperidinylalkyl, piperidinylalkyl, alkylpyrrolidinylalkyl or alkylaminoalkyl; more preferably, $R_1$ is H or $CH_3$; more preferably, $R_1$ is $CH_3$;

$R_2$ is H, formyl, halo, amino, alkylamino or alkyl; wherein alkyl is optionally substituted by at least one group selected from hydroxyl, amino, alkylamino, aryl, heteroaryl, alkylaryl, alkylheteroaryl, cycloalkyl, heterocycloalkyl, alkylcycloalkyl or alkylheterocycloalkyl; preferably $R_2$ is H, formyl, Br, $CH_3$, $CH_2OH$, alkylpiperazine, methylpiperazinylmethyl or alkylamino; more preferably, $R_2$ is H or $CH_3$;

$R_3$ and $R_4$ are identical or different and each one is selected from the group of amido, alkyl, carboxyl, hydroxyl, heterocycloalkyloxo, cycloalkyloxo or formyl, or $R_3$ and $R_4$ are fused together to form a cycloalkyl or heterocycloalkyl group, optionally substituted by at least one alkylaryl, alkylheteroaryl, nitroaryl, nitroheteroaryl, alkoxyaryl or alkoxyheteroaryl; wherein alkyl, heterocycloalkyloxo or cycloalkyloxo is optionally substituted by at least one group selected from alkyl, hydroxyl, carboxyl, oxo, amido, amino and formyl; wherein amido is optionally substituted by at least one group selected from alkyl, ester, heteroalkyl, hydroxyl, arylalkyl or alkylaryl, said group being optionally substituted by at least one group selected from alkyl, heteroalkyl, alkoxyl, hydroxyl or ester; preferably $R_3$ and $R_4$ are identical and represent $CH_2OH$; or $R_3$ is $CH_3$ and $R_4$ is carboxyl; or $R_3$ is carboxyl and $R_4$ is $CH_3$; or $R_3$ and $R_4$ are fused to form 2-(4-nitrophenyl)-1,3-dioxane or 2-(3,4-dimethoxyphenyl)-1,3-dioxane; and R' is H, formyl, alkyl or alkylcarbonyl group optionally substituted by alkyl, carboxyl or hydroxyl; preferably, R' is H, formyl or carboxylalkylcarbonyl.

In one embodiment, —OR' represents —OH, —OCOH or —OCO(CH$_2$)$_2$COOH.

According to one embodiment, preferred compounds of formula (I) are compounds of formula (I'):

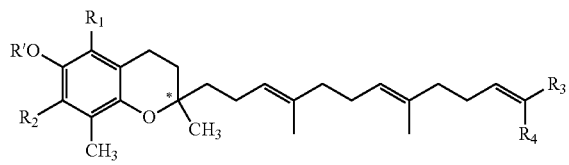

and pharmaceutically acceptable salts and/or solvates thereof, wherein:

* stands for the (R)-enantiomer, the (S)-enantiomer, for the racemate or for the non racemic mixture of (R) and (S) enantiomers of the corresponding formula (I');

R', R$_1$ and R$_2$ are as defined in formula (I); and

R$_3$ and R$_4$ are identical or different and each one is selected from the group of amido, alkyl, carboxyl, hydroxyl or formyl, or R$_3$ and R$_4$ are fused together to form a cycloalkyl or heterocycloalkyl group, optionally substituted by at least one alkylaryl, alkylheteroaryl, nitroaryl, nitroheteroaryl, alkoxyaryl or alkoxyheteroaryl; wherein alkyl is optionally substituted by at least one group selected from hydroxyl, carboxyl, oxo, amido, amino and formyl; wherein amido is optionally substituted by at least one group selected from alkyl, arylalkyl or alkylaryl; preferably R$_3$ and R$_4$ are identical and represent CH$_2$OH; or R$_3$ is CH$_3$ and R$_4$ is carboxyl; or R$_3$ is carboxyl and R$_4$ is CH$_3$; or R$_3$ and R$_4$ are fused to form 2-(4-nitrophenyl)-1,3-dioxane or 2-(3,4-dimethoxyphenyl)-1,3-dioxane.

Without willing to be bound by any theory, the Applicant has suggested that an unsaturated side chain improves the passage of the lipid barrier. The results obtained by the Applicant support this theory.

According to one embodiment, compound of formula (I) is not one of the following compounds:

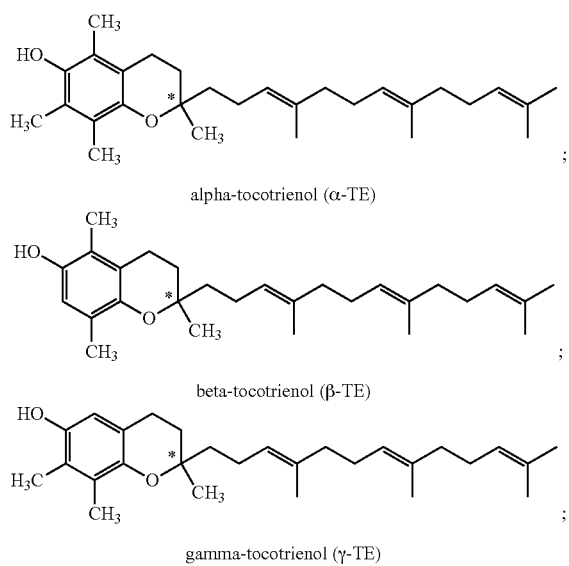

alpha-tocotrienol (α-TE)

beta-tocotrienol (β-TE)

gamma-tocotrienol (γ-TE)

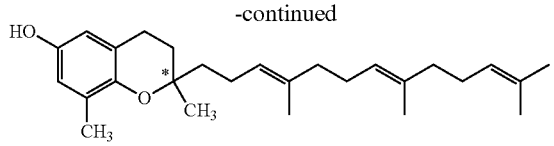

delta-tocotrienol (δ-TE)

According to one embodiment, compound of formula (I) or of formula (I') does not comprise compound of formula:

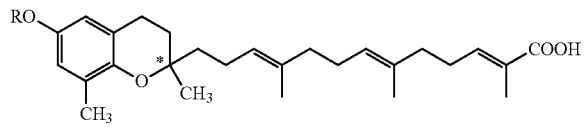

wherein R is selected from —H, —CH$_3$ or —CO—CH$_3$.

In one specific embodiment, compound of formula (I) or of formula (I') does not comprise δ-garcinoic acid. In one specific embodiment, compound of formula (I) or of formula (I') does not comprise δ-tocotrienol derivatives.

In one specific embodiment, R$_1$ is not H. In one specific embodiment, R$_1$ and R$_2$ are not both H.

In one specific embodiment, compounds of formula (I) or of formula (I') do not comprise compounds wherein R$_3$ or R$_4$ is carboxyl.

In one specific embodiment, R$_1$ is H, formyl, amino, alkylamino or unsubstituted alkyl. In one embodiment, R$_1$ is H, formyl, amino, alkylamino or unsubstituted C1-C6 alkyl. In one specific embodiment, R$_1$ is H, formyl, amino, alkylamino, methyl, ethyl, propyl, butyl, pentyl or hexyl.

In one embodiment, R$_1$ is H, formyl, amino, alkylamino, methyl, ethyl, propyl, butyl or pentyl. In one embodiment, R$_1$ is H, formyl, amino, alkylamino, methyl, ethyl, propyl or butyl. In one embodiment, R$_1$ is H, formyl, amino, alkylamino, methyl, ethyl or propyl. In one embodiment, R$_1$ is H, formyl, amino, alkylamino, methyl or ethyl. In one embodiment, R$_1$ is H, formyl, amino, alkylamino or methyl.

In one specific embodiment, R$_1$ is H, formyl, amino, alkylamino or alkyl substituted by at least one group selected from hydroxyl, amino, alkylamino, aryl, heteroaryl, alkylaryl or alkylheteroaryl.

In one embodiment, R$_1$ is H, formyl, amino, alkylamino or C1-C6 alkyl substituted by at least one group selected from hydroxyl, amino, alkylamino, aryl, heteroaryl, alkylaryl or alkylheteroaryl.

In one embodiment, R$_1$ is H, formyl, amino, alkylamino or alkyl substituted by at least one group selected from hydroxyl, amino, alkylamino, alkylpiperazinyl, alkylmorpholino, morpholino, piperidinyl, alkylpiperidinyl, alkylpyrrolidinyl or alkylamino.

In one embodiment, R$_1$ is H, formyl, amino, alkylamino or C1-C6 alkyl substituted by at least one group selected from hydroxyl, amino, alkylamino, alkylpiperazinyl, alkylmorpholino, morpholino, piperidinyl, alkylpiperidinyl, alkylpyrrolidinyl or alkylamino. In one embodiment, R$_1$ is H, formyl, CH$_3$, alkylpiperazinylalkyl, alkylmorpholinoalkyl, morpholinoalkyl, piperidinylalkyl, alkylpiperidinylalkyl, alkylpyrrolidinylalkyl or alkylaminoalkyl. In one embodiment, R$_1$ is H, formyl, CH$_3$, methylpiperazinylmethyl, morpholinomethyl, piperidinylmethyl, pyrrolidinylmethyl or dimethylaminomethyl.

In another specific embodiment, R$_1$ is H or CH$_3$. In one embodiment, R$_1$ is H. In one embodiment, R$_1$ is CH$_3$.

In one specific embodiment, $R_2$ is H, formyl, halo, amino, alkylamino or unsubstituted alkyl. In one embodiment, $R_2$ is H, formyl, halo, amino, alkylamino or unsubstituted C1-C6 alkyl. In one embodiment, $R_2$ is H, formyl, halo, amino, alkylamino, methyl, ethyl, propyl, butyl, pentyl or hexyl. In one embodiment, $R_2$ is H, formyl, halo, amino, alkylamino, methyl, ethyl, propyl, butyl or pentyl. In one embodiment, $R_2$ is H, formyl, halo, amino, alkylamino, methyl, ethyl, propyl or butyl. In one embodiment, $R_2$ is H, formyl, halo, amino, alkylamino, methyl, ethyl or propyl. In one embodiment, $R_2$ is H, formyl, halo, amino, alkylamino, methyl or ethyl. In one embodiment, $R_2$ is H, formyl, halo, amino, alkylamino or methyl.

In one specific embodiment, $R_2$ is H, formyl, halo, amino, alkylamino or alkyl substituted by at least one group selected from hydroxyl, amino, alkylamino, aryl, heteroaryl, alkylaryl or alkylheteroaryl. In one embodiment, $R_2$ is H, formyl, halo, amino, alkylamino or C1-C6 alkyl substituted by at least one group selected from hydroxyl, amino, alkylamino, aryl, heteroaryl, alkylaryl or alkylheteroaryl. In one embodiment, $R_2$ is H, formyl, Br, $CH_3$, $CH_2OH$, alkylpiperazine or alkylamino In one embodiment, $R_2$ is H, formyl, Br, $CH_3$, $CH_2OH$, methylpiperazinylmethyl or dimethylaminomethyl.

In one specific embodiment, $R_2$ is F, Cl, Br or I. In one embodiment, $R_2$ is Br. In one embodiment, $R_2$ is Cl. In one embodiment, $R_2$ is F. In one embodiment, $R_2$ is I.

In another specific embodiment, $R_2$ is H or $CH_3$. In one embodiment, $R_2$ is H. In one embodiment, $R_2$ is $CH_3$.

In one specific embodiment, $R_3$ and $R_4$ are identical and each one is selected from the group of amido, alkyl, carboxyl, hydroxyl and formyl; said alkyl group being optionally substituted by at least one group selected from hydroxyl, carboxyl, oxo, amido, amino and formyl; said amido group being optionally substituted by at least one group selected from alkyl, arylalkyl or alkylaryl. In one embodiment, $R_3$ and $R_4$ are identical and each one is selected from an alkyl group substituted by one hydroxyl group. In one embodiment, $R_3$ and $R_4$ are identical and are both $CH_2OH$. In one embodiment, $R_3$ and $R_4$ are identical and are both methyl.

In one specific embodiment, $R_3$ and $R_4$ are different and each one is selected from the group of amido, alkyl, carboxyl, hydroxyl and formyl; said alkyl group being optionally substituted by at least one group selected from hydroxyl, carboxyl, oxo, amido, amino and formyl; said amido group being optionally substituted by at least one group selected from alkyl, arylalkyl or alkylaryl. In one embodiment, $R_3$ is an alkyl group and $R_4$ is a carboxyl group. In one embodiment, $R_3$ is a carboxyl group and $R_4$ is an alkyl group. In one embodiment, $R_3$ is methyl and $R_4$ is a carboxyl group. In one embodiment, $R_3$ is a carboxyl group and $R_4$ is methyl. In one embodiment, $R_3$ is an alkyl group and $R_4$ is an amido group substituted by arylalkyl or alkylaryl. In one embodiment, $R_3$ is an amido group substituted by arylalkyl or alkylaryl and $R_4$ is an alkyl group. In one embodiment, $R_3$ is methyl and $R_4$ is an amido group substituted by a benzyl group. In one embodiment, $R_3$ is an amido group substituted by a benzyl group and $R_4$ is methyl. In one embodiment, $R_3$ is an alkyl group substituted by at least one hydroxyl group and $R_4$ is an unsubstituted alkyl group. In one embodiment, $R_3$ is an unsubstituted alkyl group and $R_4$ is an alkyl group substituted by at least one hydroxyl group. In one embodiment, $R_3$ is $CH_2OH$ and $R_4$ is methyl. In one embodiment, $R_3$ is methyl and $R_4$ is $CH_2OH$. In one embodiment, $R_3$ is a formyl group and $R_4$ is $CH_2OH$. In one embodiment, $R_3$ is a $CH_2OH$ and $R_4$ is a formyl group. In one embodiment, $R_3$ and $R_4$ are both $CH_2OH$.

In one specific embodiment, $R_3$ and $R_4$ are fused together to form a cycloalkyl or heterocycloalkyl group. In one embodiment, $R_3$ and $R_4$ are fused together to form a dioxane. In one embodiment, $R_3$ and $R_4$ are fused together to form a 1,2-dioxane. In one embodiment, $R_3$ and $R_4$ are fused together to form a 1,3-dioxane. In one embodiment, $R_3$ and $R_4$ are fused together to form a 1,4-dioxane. In one embodiment, $R_3$ and $R_4$ are fused together to form a dioxane substituted by at least one alkylaryl, alkylheteroaryl, nitroaryl, nitroheteroaryl, alkoxyaryl or alkoxyheteroaryl. In one embodiment, $R_3$ and $R_4$ are fused together to form a dioxane substituted by only one alkylaryl, alkylheteroaryl, nitroaryl, nitroheteroaryl, alkoxyaryl or alkoxyheteroaryl. In one embodiment, $R_3$ and $R_4$ are fused together to form a nitrophenyl-1,3-dioxane; preferably 2-(4-nitrophenyl)-1,3-dioxane. In one embodiment, $R_3$ and $R_4$ are fused together to form a dimethoxyphenyl-1,3-dioxane; preferably 2-(3,4-dimethoxyphenyl)-1,3-dioxane.

In one specific embodiment, at least one of $R_3$ or $R_4$ represents an oxidized group or a group having an oxidized function. In one embodiment, at least one of $R_3$ or $R_4$ represents an oxidized group or a group having an oxidized function selected from hydroxyl, formyl or carboxyl. In one embodiment, $R_3$ and $R_4$ both represent an oxidized group or a group having an oxidized function selected from hydroxyl, formyl or carboxyl. In one embodiment, $R_3$ and $R_4$ are identical and represent an oxidized group or a group having an oxidized function selected from hydroxyl, formyl or carboxyl.

In one embodiment, $R_3$ and $R_4$ are selected such that the stereochemistry of double bond C=C to which they are attached is (Z). In one embodiment, $R_3$ and $R_4$ are selected such that the stereochemistry of double bond C=C to which they are attached is (E).

In one specific embodiment, compound of formula (I) is the (R)-enantiomer. In one embodiment, compound of formula (I) is the (S)-enantiomer. In one embodiment, compound of formula (I) is the racemate.

In one embodiment, preferred compounds of formula (I') are those of formula (Ia):

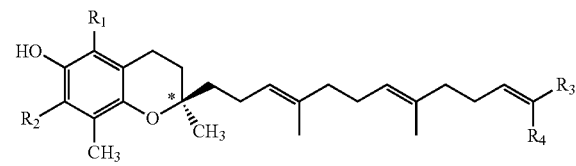

and pharmaceutically acceptable salts and/or solvates thereof, wherein $R_1$, $R_2$, $R_3$ and $R_4$ are as defined in formula (I').

In one embodiment, preferred compounds of formula (I') are those of formula (Ib):

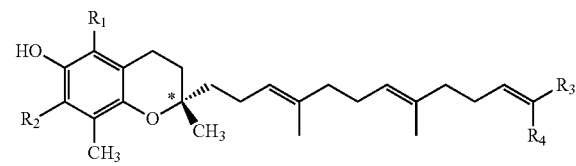

and pharmaceutically acceptable salts and/or solvates thereof, wherein $R_1$, $R_2$, $R_3$ and $R_4$ are as defined in formula (I').

In one specific embodiment, preferred compounds of formula (I') are those of formula (II):

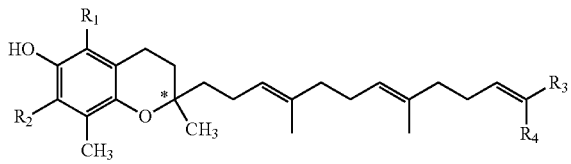

and pharmaceutically acceptable salts and/or solvates thereof, wherein:
* stands for the (R)-enantiomer, the (S)-enantiomer, for the racemate or for the non racemic mixture of (R) and (S) enantiomers of the corresponding formula (II);
$R_1$ and $R_2$ are as defined in formula (I');
$R_3$ and $R_4$ are identical or different and each one is selected from the group of amido, alkyl, carboxyl, hydroxyl and formyl; wherein alkyl is optionally substituted by at least one group selected from hydroxyl, carboxyl, oxo, amido, amino and formyl; wherein amido group is optionally substituted by at least one group selected from alkyl, arylalkyl or alkylaryl; preferably $R_3$ and $R_4$ are identical and represent $CH_2OH$; preferably $R_3$ is $CH_3$ and $R_4$ is carboxyl; preferably $R_3$ is carboxyl and $R_4$ is $CH_3$; and wherein at least one of $R_3$ or $R_4$ is an alkyl substituted by at least one group selected from hydroxyl, carboxyl or formyl.

In one specific embodiment, $R_1$ is not H. In one specific embodiment, $R_1$ and $R_2$ are not both H.

In one embodiment, preferred compounds of formula (I') are those of formula (III):

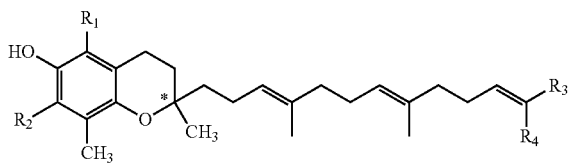

and pharmaceutically acceptable salts and/or solvates thereof, wherein:
* stands for the (R)-enantiomer, the (S)-enantiomer, for the racemate or for the non racemic mixture of (R) and (S) enantiomers of the corresponding formula (III);
$R_1$ is H or alkyl; preferably $R_1$ is H or C1-C6 alkyl; more preferably, $R_1$ is $CH_3$;
$R_2$ is H or alkyl; preferably, $R_2$ is H or C1-C6 alkyl; more preferably, $R_2$ is H or $CH_3$;
$R_3$ and $R_4$ are identical or different and each one is selected from the group of amido, alkyl, carboxyl, hydroxyl and formyl; wherein alkyl is optionally substituted by at least one group selected from hydroxyl, carboxyl, oxo, amido, amino and formyl; wherein amido group is optionally substituted by at least one group selected from alkyl, arylalkyl or alkylaryl; preferably $R_3$ and $R_4$ are identical and represent $CH_2OH$; preferably $R_3$ is $CH_3$ and $R_4$ is carboxyl; preferably $R_3$ is carboxyl and $R_4$ is $CH_3$; and wherein at least one of $R_3$ or $R_4$ is an alkyl substituted by at least one group selected from hydroxyl, carboxyl or formyl.

In one specific embodiment, $R_1$ is not H.
In one specific embodiment, $R_1$ and $R_2$ are not both H.
In one specific embodiment, when $R_3$ is COOH and $R_4$ is H, $R_1$ and $R_2$ are not both H.

In one specific embodiment, compound of formula (III) is the (R)-enantiomer. In one specific embodiment, compound of formula (III) is the (S)-enantiomer. In one specific embodiment, compound of formula (III) is the racemate.

In one embodiment, preferred compounds of formula (III) are those of formula (IIIa):

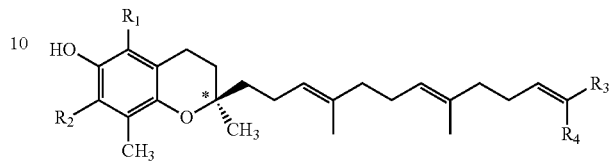

and pharmaceutically acceptable salts and/or solvates thereof, wherein $R_1$, $R_2$, $R_3$ and $R_4$ are as defined in formula (III).

In one embodiment, preferred compounds of formula (III) are those of formula (IIIb):

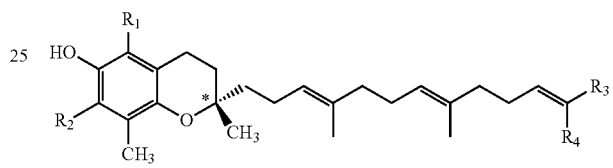

and pharmaceutically acceptable salts and/or solvates thereof, wherein $R_1$, $R_2$, $R_3$ and $R_4$ are as defined in formula (III).

In one embodiment, preferred compounds of formula (IIIa) are those wherein $R_1$ is $CH_3$.
In one embodiment, preferred compounds of formula (IIIb) are those wherein $R_1$ is $CH_3$.
In one embodiment, preferred compounds of formula (III) are those of formula (IV):

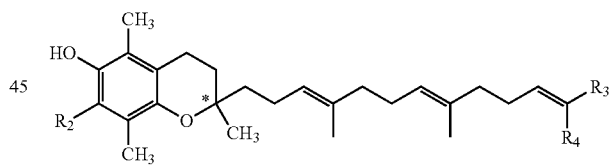

and pharmaceutically acceptable salts and/or solvates thereof, wherein:
* stands for the (R)-enantiomer, the (S)-enantiomer, for the racemate or for the non racemic mixture of (R) and (S) enantiomers of the corresponding formula (IV); and
$R_2$, $R_3$ and $R_4$ are as defined in formula (III).

In one embodiment, the oxidized group or a group having an oxidized function is selected from —$CH_2OH$, —OH or —COOH.

In one embodiment, preferred compounds of formula (IV) are selected from those wherein:
$R_2$ is H; $R_3$ is $CH_2OH$ and $R_4$ is $CH_2OH$;
$R_2$ is $CH_3$; $R_3$ is $CH_2OH$ and $R_4$ is $CH_2OH$;
$R_2$ is H; $R_3$ is $CH_3$ and $R_4$ is COOH;
$R_2$ is H; $R_3$ is COOH and $R_4$ is $CH_3$;
$R_2$ is $CH_3$; $R_3$ is $CH_3$ and $R_4$ is COOH;
$R_2$ is $CH_3$; $R_3$ is COOH and $R_4$ is $CH_3$.

In one embodiment, preferred compounds of formula (IV) are those wherein $R_3$ and $R_4$ are selected such that the stereochemistry of double bond C=C to which they are attached is (Z). In one embodiment, preferred compounds of formula (IV) are those wherein $R_3$ and $R_4$ are selected such that the stereochemistry of double bond C=C to which they are attached is (E).

In one embodiment, preferred compounds of formula (III) are those of formula (V):

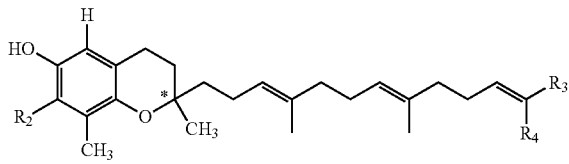

and pharmaceutically acceptable salts and/or solvates thereof, wherein:
* stands for the (R)-enantiomer, the (S)-enantiomer, for the racemate or for the non racemic mixture of (R) and (S) enantiomers of the corresponding formula (V);
$R_2$ is H or alkyl; preferably, $R_2$ is H or C1-C6 alkyl; more preferably, $R_2$ is H or $CH_3$;
$R_3$ and $R_4$ are identical or different and each one is selected from the group of amido, alkyl, carboxyl, hydroxyl and formyl; wherein alkyl is optionally substituted by at least one group selected from hydroxyl, carboxyl, oxo, amido, amino and formyl; wherein amido group is optionally substituted by at least one group selected from alkyl, arylalkyl or alkylaryl; preferably $R_3$ and $R_4$ are identical and represent $CH_2OH$; preferably $R_3$ is $CH_3$ and $R_4$ is carboxyl; preferably $R_3$ is carboxyl and $R_4$ is $CH_3$; and wherein at least one of $R_3$ or $R_4$ is an alkyl substituted by at least one group selected from hydroxyl, carboxyl or formyl.

In one specific embodiment, $R_2$ is not H. In one specific embodiment, $R_2$ is not H when $R_3$ is COOH and $R_4$ is $CH_3$.

In one embodiment, preferred compounds of formula (I') are those of formula (VI):

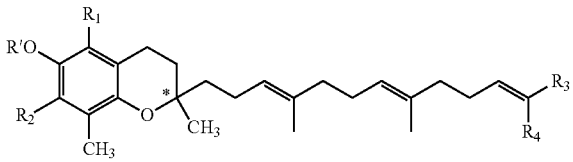

and pharmaceutically acceptable salts and/or solvates thereof,
* stands for the (R)-enantiomer, the (S)-enantiomer, for the racemate or for the non racemic mixture of (R) and (S) enantiomers of the corresponding formula (I').
wherein:
$R_1$, $R_2$ and R' are as in formula (I');
$R_3$ and $R_4$ are fused together to form a cycloalkyl or heterocycloalkyl group, optionally substituted by at least one alkylaryl, alkylheteroaryl, nitroaryl, nitroheteroaryl, alkoxyaryl or alkoxyheteroary, wherein alkyl is optionally substituted by at least one group selected from hydroxyl, carboxyl, oxo, amido, amino and formyl; preferably $R_3$ and $R_4$ are fused to form 2-(4-nitrophenyl)-1,3-dioxane or 2-(3,4-dimethoxyphenyl)-1,3-dioxane.

According to one embodiment, preferred compounds of formula (VI) are compounds of formula (VII):

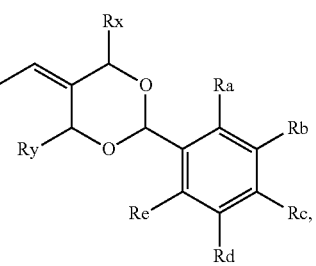

wherein:
$R_1$, $R_2$ and R' are as defined above;
$R_x$ and $R_y$ are identical or different, and each is selected from alkylaryl, alkylheteroaryl, nitroaryl, nitroheteroaryl, alkoxyaryl or alkoxyheteroaryl; wherein alkyl is optionally substituted by at least one group selected from hydroxyl, carboxyl, oxo, amido, amino and formyl;
$R_a$, $R_b$, $R_c$, $R_d$ and $R_e$ are selected from H, alkyl or alkoxy; wherein alkyl is optionally substituted by at least one group selected from hydroxyl, carboxyl, oxo, amido, amino and formyl.

According to one embodiment, preferred compounds of formula (VI) are compounds wherein $R_x$ and $R_y$ are identical and represent H.

According to one embodiment, preferred compounds of formula (VI) are compounds wherein $R_x$ and $R_y$ are identical and represent H; and $R_a$ and $R_e$ are H.

According to one embodiment, preferred compounds of formula (VI) is the compound wherein;
$R_x$ and $R_y$ are identical and represent H; and
$R_a$, $R_b$, $R_d$ and $R_e$ are H.

According to one embodiment, preferred compounds of formula (VI) are compounds wherein $R_c$ is nitro.

According to one embodiment, preferred compounds of formula (VI) are compounds wherein $R_b$ or $R_d$ is alkoxy; preferably C1-C6 alkoxy; more preferably, methoxy.

Particularly preferred compounds of formula (I) of the invention are those listed in Table 1 hereafter, together with reference compound which is δ-garcinoic acid (compound 27):

TABLE 1

| Cpd n° | Structure | Chemical name | MW |
|---|---|---|---|
| 1 | 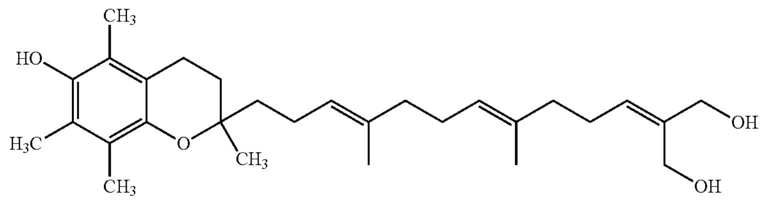 [SMILES: C/C(=C\CC/C(C)=C/CCC1(C)CCc2c(C)c(O)c(C)c(C)c2O1)CCC=C(CO)CO] | 2-((4E,8E)-11-(6-hydroxy-2,5,7,8-tetramethylchroman-2-yl)-4,8-dimethylundeca-4,8-dien-1-ylidene)propane-1,3-diol | 456.26 |
| 2 | 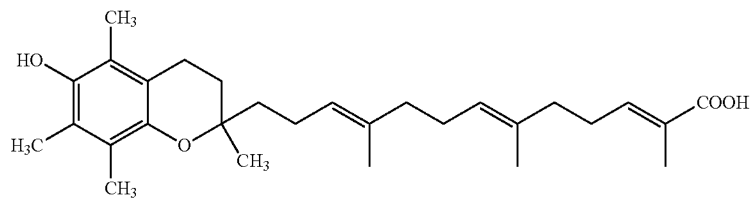 [SMILES: C/C(=C\CC/C(C)=C/CCC1(C)CCc2c(C)c(O)c(C)c(C)c2O1)CC/C=C(\C)C(=O)O] | (2E,6E,10E)-13-(6-hydroxy-2,5,7,8-tetramethylchroman-2-yl)-2,6,10-trimethyltrideca-2,6,10-trienoic acid | 454.64 |
| 3 | 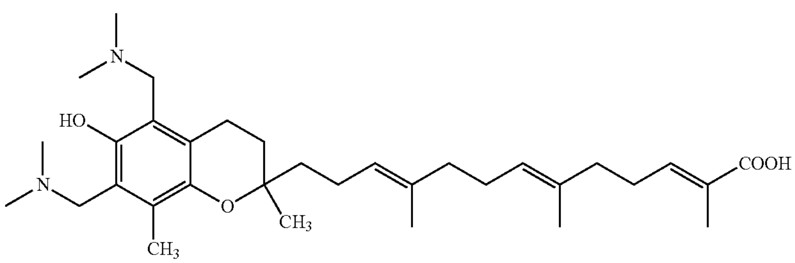 [SMILES: C/C(=C\CC/C(C)=C/CCC1(C)CCc2c(CN(C)C)c(O)c(CN(C)C)c(C)c2O1)CC/C=C(\C)C(=O)O] | (2E,6E,10E)-13-(5,7-bis((dimethylamino)methyl)-6-hydroxy-2,8-dimethylchroman-2-yl)-2,6,10-trimethyltrideca-2,6,10-trienoic acid | 540.78 |
| 4 | 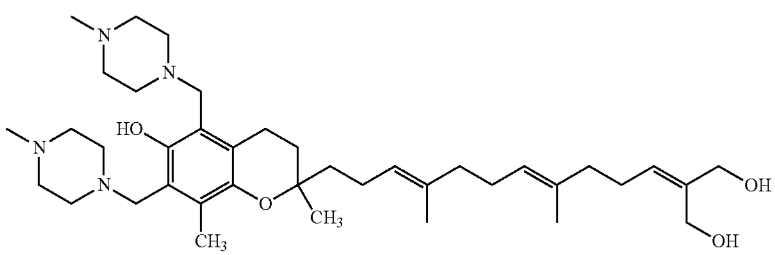 [SMILES: C/C(=C\CC/C(C)=C/CCC1(C)CCc2c(CN3CCN(C)CC3)c(O)c(CN3CCN(C)CC3)c(C)c2O1)CCC=C(CO)CO] | 2-((4E,8E)-11-(6-hydroxy-2,8-dimethyl-5,7-bis((4-methylpiperazin-1-yl)methyl)chroman-2-yl)-4,8-dimethylundeca-4,8-dien-1-ylidene)propane-1,3-diol | 652.49 |
| 5 | 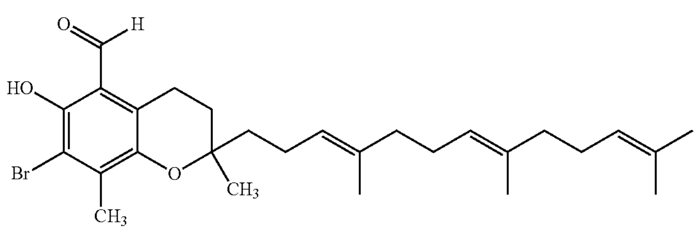 [SMILES: CC(C)=CCC/C(C)=C/CC/C(C)=C/CCC1(C)CCc2c(C=O)c(O)c(Br)c(C)c2O1] | 7-bromo-6-hydroxy-2,8-dimethyl-2-((3E,7E)-4,8,12-trimethyltrideca-3,7,11-trien-1-yl)chroman-5-carbaldehyde | 503.51 |
| 6 | 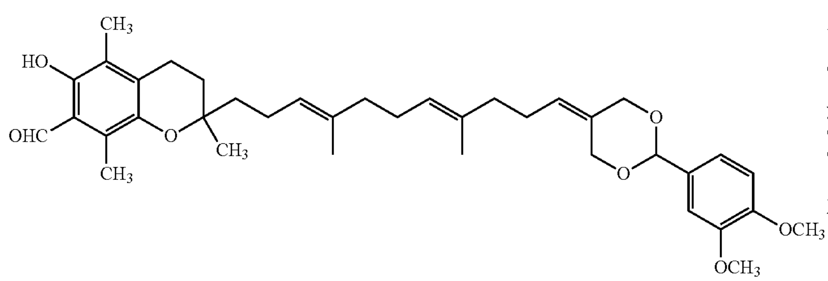 [SMILES: COc1ccc(C2OCC(=CCC/C(C)=C/CC/C(C)=C/CCC3(C)CCc4c(C)c(O)c(C=O)c(C)c4O3)CO2)cc1OC] | 2-((3E,7E)-11-(2-(3,4-dimethoxyphenyl)-1,3-dioxan-5-ylidene)-4,8-dimethylundeca-3,7-dien-1-yl)-7-(hydroxymethyl)-2,5,8-trimethylchroman-6-ol | 620.37 |

TABLE 1-continued

| Cpd n° | Structure | Chemical name | MW |
|---|---|---|---|
| 7 | 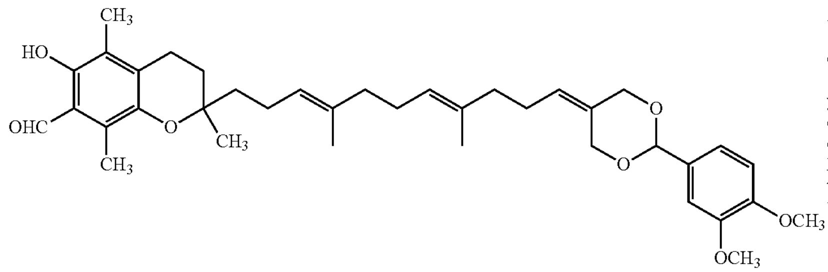 [SMILES: COc1ccc(C2OCC(=CCC/C(C)=C/CC/C(C)=C/CCC3(C)CCc4c(C)c(O)c(C=O)c(C)c4O3)CO2)cc1OC] | 2-((3E,7E)-11-(2-(3,4-dimethoxyphenyl)-1,3-dioxan-5-ylidene)-4,8-dimethylundeca-3,7-dien-1-yl)-6-hydroxy-2,5,8-trimethylchroman-7-carbaldehyde | 618.36 |
| 8 | 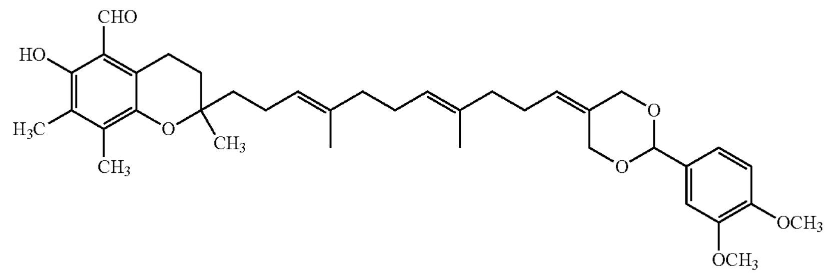 [SMILES: COc1ccc(C2OCC(=CCC/C(C)=C/CC/C(C)=C/CCC3(C)CCc4c(C=O)c(O)c(C)c(C)c4O3)CO2)cc1OC] | 2-((3E,7E)-11-(2-(3,4-dimethoxyphenyl)-1,3-dioxan-5-ylidene)-4,8-dimethylundeca-3,7-dien-1-yl)-6-hydroxy-2,7,8-trimethylchroman-5-carbaldehyde | 618.36 |
| 9 | 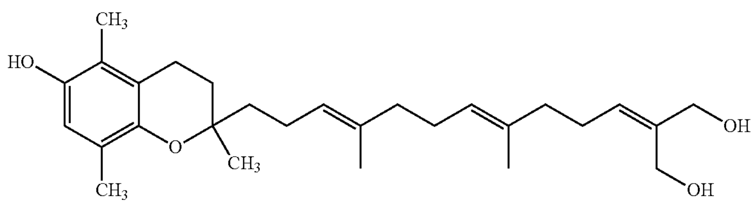 [SMILES: C/C(=C\CC/C(C)=C/CCC1(C)CCc2c(C)c(O)cc(C)c2O1)CCC=C(CO)CO] | 2-((4E,8E)-11-(6-hydroxy-2,5,8-trimethylchroman-2-yl)-4,8-dimethylundeca-4,8-dien-1-ylidene)propane-1,3-diol | 442.31 |
| 10 | 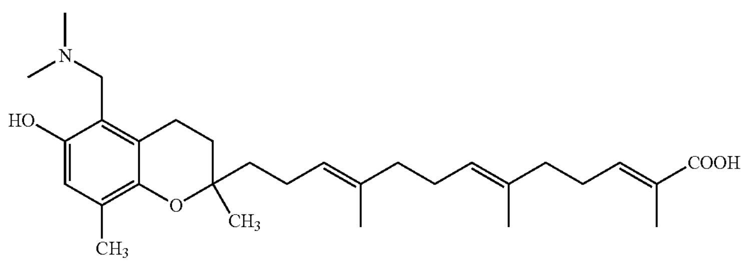 [SMILES: C/C(=C\CC/C(C)=C/CCC1(C)CCc2c(CN(C)C)c(O)cc(C)c2O1)CC/C=C(\C)C(=O)O] | (2E,6E,10E)-13-(5-((dimethylamino)methyl)-6-hydroxy-2,8-dimethylchroman-2-yl)-2,6,10-trimethyltrideca-2,6,10-trienoic acid | 483.33 |
| 11 | 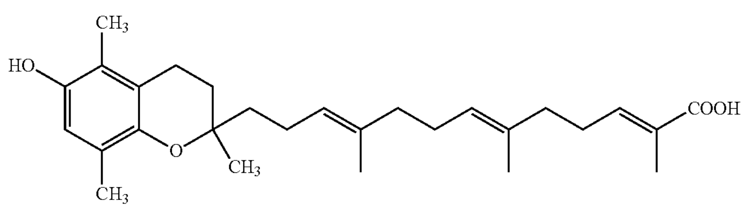 [SMILES: C/C(=C\CC/C(C)=C/CCC1(C)CCc2c(C)c(O)cc(C)c2O1)CC/C=C(\C)C(=O)O] | (2E,6E,10E)-13-(6-hydroxy-2,5,8-trimethylchroman-2-yl)-2,6,10-trimethyltrideca-2,6,10-trienoic acid | 440.29 |
| 12 | 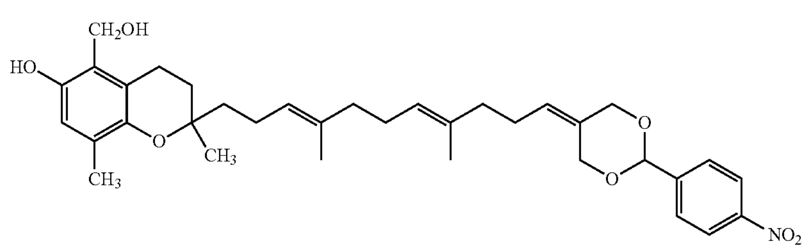 [SMILES: C/C(=C\CC/C(C)=C/CCC1(C)CCc2c(CO)c(O)cc(C)c2O1)CCC=C1COC(c2ccc([N+](=O)[O-])cc2)OC1] | 2-((3E,7E)-4,8-dimethyl-11-(2-(4-nitrophenyl)-1,3-dioxan-5-ylidene)undeca-3,7-dien-1-yl)-5-(hydroxymethyl)-2,8-dimethylchroman-6-ol | 591.32 |

TABLE 1-continued

| Cpd n° | Structure | Chemical name | MW |
|---|---|---|---|
| 13 | 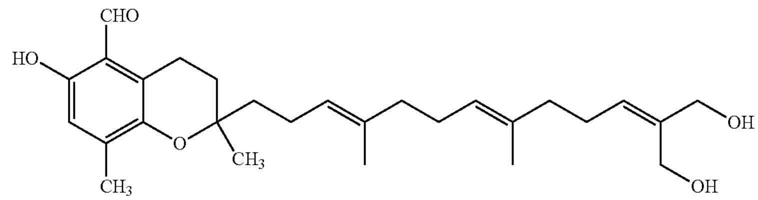 [SMILES: C/C(=C\CC/C(C)=C/CCC1(C)CCc2c(C=O)c(O)cc(C)c2O1)CCC=C(CO)CO] | 6-hydroxy-2-((3E,7E)-13-hydroxy-12-(hydroxymethyl)-4,8-dimethyltrideca-3,7,11-trien-1-yl)-2,8-dimethylchroman-5-carbaldehyde | 456.29 |
| 14 | 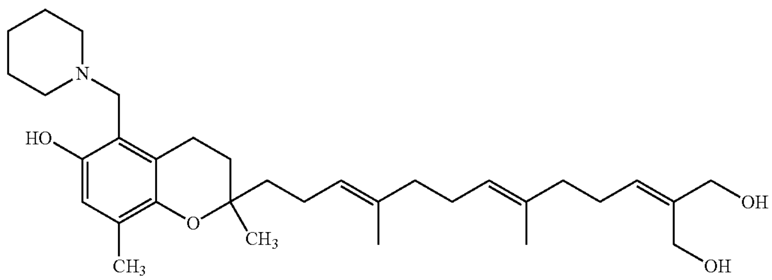 [SMILES: C/C(=C\CC/C(C)=C/CCC1(C)CCc2c(CN3CCCCC3)c(O)cc(C)c2O1)CCC=C(CO)CO] | 2-((4E,8E)-11-(6-hydroxy-2,8-dimethyl-5-(piperidin-1-ylmethyl)chroman-2-yl)-4,8-dimethylundeca-4,8-dien-1-ylidene)propane-1,3-diol | 525.38 |
| 15 | 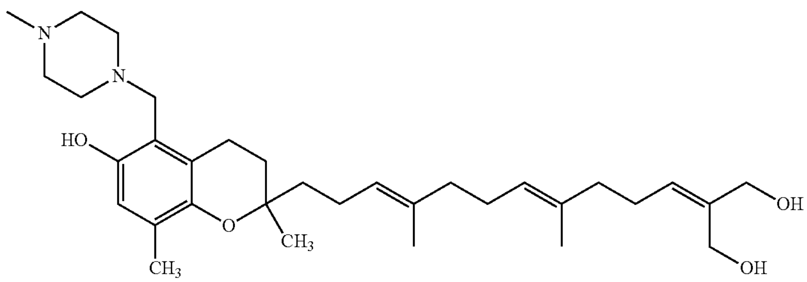 [SMILES: C/C(=C\CC/C(C)=C/CCC1(C)CCc2c(CN3CCN(C)CC3)c(O)cc(C)c2O1)CCC=C(CO)CO] | 2-((4E,8E)-11-(6-hydroxy-2,8-dimethyl-5-((4-methylpiperazin-1-yl)methyl)chroman-2-yl)-4,8-dimethylundeca-4,8-dien-1-ylidene)propane-1,3-diol | 540.39 |
| 16 | 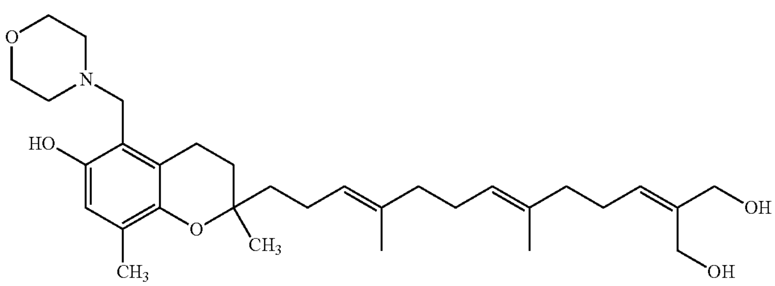 [SMILES: C/C(=C\CC/C(C)=C/CCC1(C)CCc2c(CN3CCOCC3)c(O)cc(C)c2O1)CCC=C(CO)CO] | 2-((4E,8E)-11-(6-hydroxy-2,8-dimethyl-5-(morpholinomethyl)chroman-2-yl)-4,8-dimethylundeca-4,8-dien-1-ylidene)propane-1,3-diol | 527.36 |
| 17 | 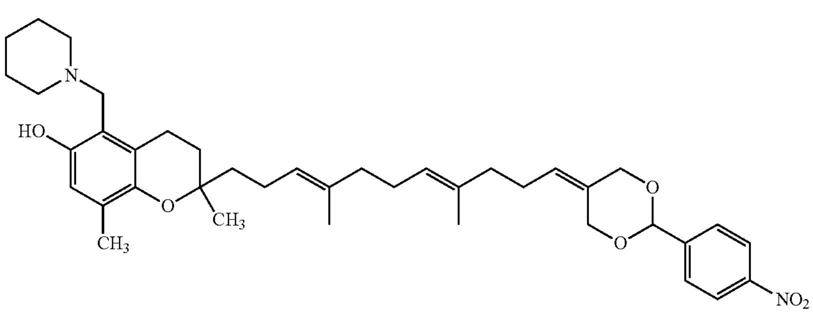 [SMILES: C/C(=C\CC/C(C)=C/CCC1(C)CCc2c(CN3CCCCC3)c(O)cc(C)c2O1)CCC=C1COC(c2ccc([N+](=O)[O-])cc2)OC1] | 2-((3E,7E)-4,8-dimethyl-11-(2-(4-nitrophenyl)-1,3-dioxan-5-ylidene)undeca-3,7-dien-1-yl)-2,8-dimethyl-5-(piperidin-1-ylmethyl)chroman-6-ol | 658.40 |

TABLE 1-continued

| Cpd n° | Structure | Chemical name | MW |
|---|---|---|---|
| 18 | 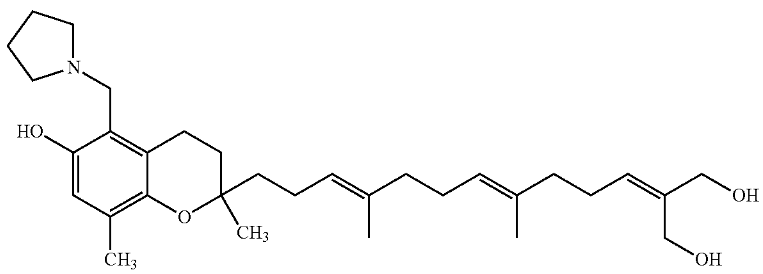 [SMILES: C/C(=C\CC/C(C)=C/CCC1(C)CCc2c(CN3CCCC3)c(O)cc(C)c2O1)CCC=C(CO)CO] | 2-((4E,8E)-11-(6-hydroxy-2,8-dimethyl-5-(pyrrolidin-1-ylmethyl)chroman-2-yl)-4,8-dimethylundeca-4,8-dien-1-ylidene)propane-1,3-diol | 511.37 |
| 19 | 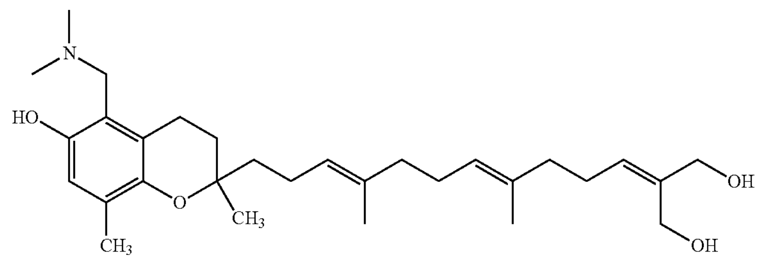 [SMILES: C/C(=C\CC/C(C)=C/CCC1(C)CCc2c(CN(C)C)c(O)cc(C)c2O1)CCC=C(CO)CO] | 2-((4E,8E)-11-(5-((dimethylamino)methyl)-6-hydroxy-2,8-dimethylchroman-2-yl)-4,8-dimethylundeca-4,8-dien-1-ylidene)propane-1,3-diol | 485.35 |
| 20 | 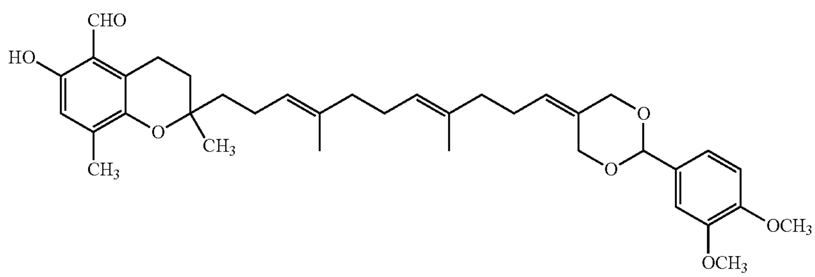 [SMILES: COc1ccc(C2OCC(=CCC/C(C)=C/CC/C(C)=C/CCC3(C)CCc4c(C=O)c(O)cc(C)c4O3)CO2)cc1OC] | 2-((3E,7E)-11-(2-(3,4-dimethoxyphenyl)-1,3-dioxan-5-ylidene)-4,8-dimethylundeca-3,7-dien-1-yl)-6-hydroxy-2,8-dimethylchroman-5-carbaldehyde | 604.34 |
| 21 | 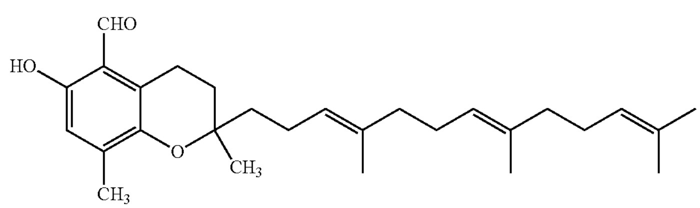 [SMILES: CC(C)=CCC/C(C)=C/CC/C(C)=C/CCC1(C)CCc2c(C=O)c(O)cc(C)c2O1] | 6-hydroxy-2,8-dimethyl-2-((3E,7E)-4,8,12-trimethyltrideca-3,7,11-trien-1-yl)chroman-5-carbaldehyde | 424.30 |
| 22 | 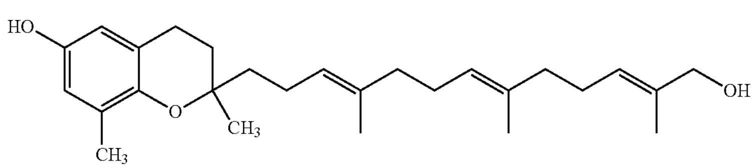 [SMILES: C/C(=C\CC/C(C)=C/CC/C(C)=C/CCC1(C)CCc2cc(O)cc(C)c2O1)CO] | 2-((3E,7E,11E)-13-hydroxy-4,8,12-trimethyltrideca-3,7,11-trien-1-yl)-2,8-dimethylchroman-6-ol | 412.30 |
| 23 | 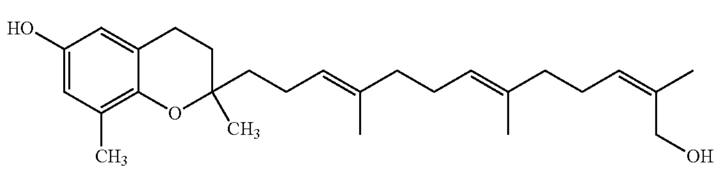 [SMILES: C/C(=C/CC/C(C)=C/CC/C(C)=C/CCC1(C)CCc2cc(O)cc(C)c2O1)CO] | 2-((3E,7E,11Z)-13-hydroxy-4,8,12-trimethyltrideca-3,7,11-trien-1-yl)-2,8-dimethylchroman-6-ol | 412.30 |
| 24 | 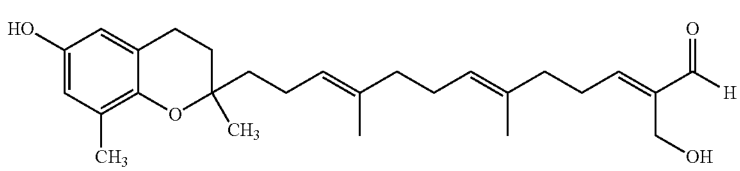 [SMILES: C/C(=C\CC/C(C)=C/CCC1(C)CCc2cc(O)cc(C)c2O1)CC/C=C(/C=O)CO] | (2E,6E,10E)-13-(6-hydroxy-2,8-dimethylchroman-2-yl)-2-(hydroxymethyl)-6,10-dimethyltrideca-2,6,10-trienal | 426.28 |

TABLE 1-continued

| Cpd n° | Structure | Chemical name | MW |
|---|---|---|---|
| 25 | 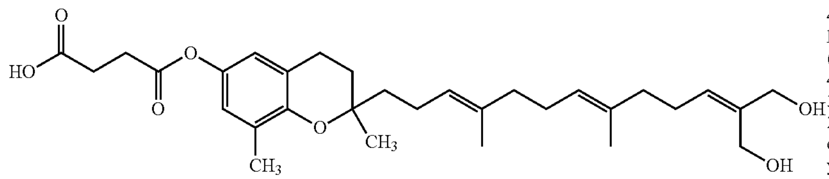 [SMILES: C/C(=C\CC/C(C)=C/CCC1(C)CCc2cc(OC(=O)CCC(=O)O)cc(C)c2O1)CCC=C(CO)CO] | 4-((2-((3E,7E)-13-hydroxy-12-(hydroxymethyl)-4,8-dimethyltrideca-3,7,11-trien-1-yl)-2,8-dimethylchroman-6-yl)oxy)-4-oxobutanoic acid | 528.31 |
| 26 | 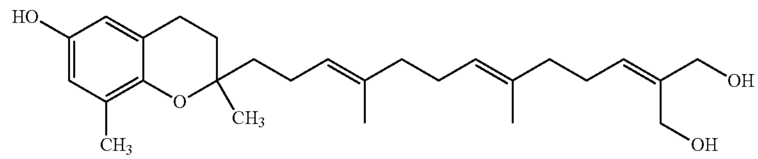 [SMILES: C/C(=C\CC/C(C)=C/CCC1(C)CCc2cc(O)cc(C)c2O1)CCC=C(CO)CO] | 2-((4E,8E)-11-(6-hydroxy-2,8-dimethylchroman-2-yl)-4,8-dimethylundeca-4,8-dien-1-ylidene)propane-1,3-diol | 428.29 |
| 27 | 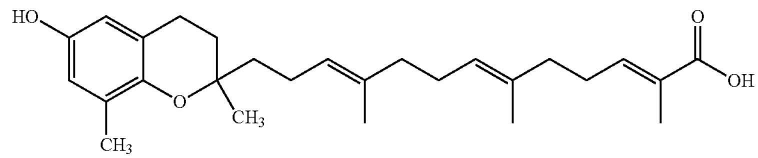 [SMILES: C/C(=C\CC/C(C)=C/CCC1(C)CCc2cc(O)cc(C)c2O1)CC/C=C(\C)C(=O)O] | (2E,6E,10E)-13-(6-hydroxy-2,8-dimethylchroman-2-yl)-2,6,10-trimethyltrideca-2,6,10-trienoic acid | 426.28 |
| 28 | 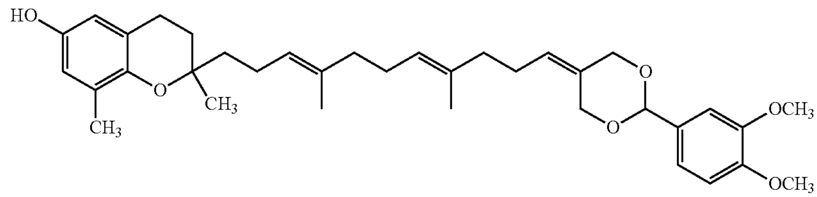 [SMILES: COc1ccc(C2OCC(=CCC/C(C)=C/CC/C(C)=C/CCC3(C)CCc4cc(O)cc(C)c4O3)CO2)cc1OC] | 2-((3E,7E)-11-(2-(3,4-dimethoxyphenyl)-1,3-dioxan-5-ylidene)-4,8-dimethylundeca-3,7-dien-1-yl)-2,8-dimethylchroman-6-ol | 576.35 |
| 29 | 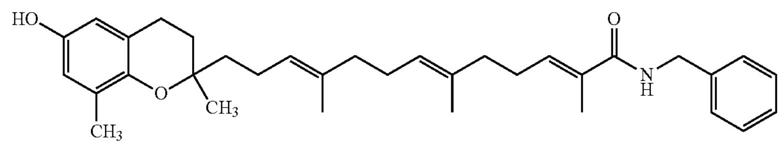 [SMILES: C/C(=C\CC/C(C)=C/CCC1(C)CCc2cc(O)cc(C)c2O1)CC/C=C(\C)C(=O)NCc1ccccc1] | (2E,6E,10E)-N-benzyl-13-(6-hydroxy-2,8-dimethylchroman-2-yl)-2,6,10-trimethyltrideca-2,6,10-trienamide | 515.34 |
| 30 | 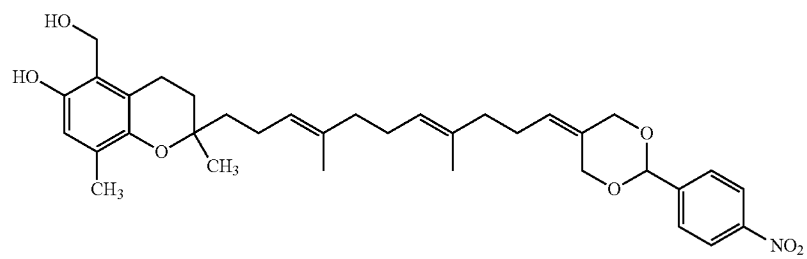 [SMILES: C/C(=C\CC/C(C)=C/CCC1(C)CCc2c(CO)c(O)cc(C)c2O1)CCC=C1COC(c2ccc([N+](=O)[O-])cc2)OC1] | 2-((3E,7E)-4,8-dimethyl-11-(2-(4-nitrophenyl)-1,3-dioxan-5-ylidene)undeca-3,7-dien-1-yl)-5-(hydroxymethyl)-2,8-dimethylchroman-6-ol | 591.32 |
| 31 | 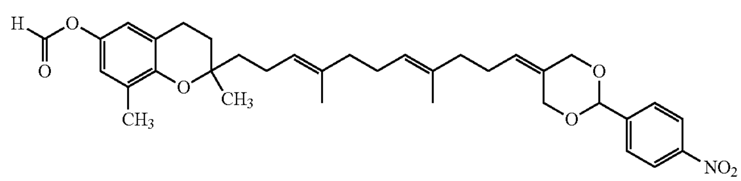 [SMILES: C/C(=C\CC/C(C)=C/CCC1(C)CCc2cc(OC=O)cc(C)c2O1)CCC=C1COC(c2ccc([N+](=O)[O-])cc2)OC1] | 2-((3E,7E)-4,8-dimethyl-11-(2-(4-nitrophenyl)-1,3-dioxan-5-ylidene)undeca-3,7-dien-1-yl)-2,8-dimethylchroman-6-yl formate | 589.30 |
| 32 | 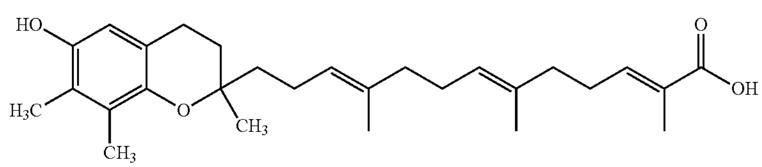 [SMILES: C/C(=C\CC/C(C)=C/CCC1(C)CCc2cc(O)c(C)c(C)c2O1)CC/C=C(\C)C(=O)O] | (2E,6E,10E)-13-(6-hydroxy-2,7,8-trimethylchroman-2-yl)-2,6,10-trimethyltrideca-2,6,10-trienoic acid | 440.29 |

TABLE 1-continued

| Cpd n° | Structure | Chemical name | MW |
|---|---|---|---|
| 33 | 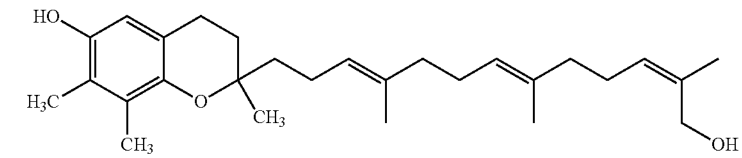 [SMILES: C/C(=C/CC/C(C)=C/CC/C(C)=C/CCC1(C)CCc2cc(O)c(C)c(C)c2O1)CO] | 2-((3E,7E,11Z)-13-hydroxy-4,8,12-trimethyltrideca-3,7,11-trien-1-yl)-2,7,8-trimethylchroman-6-ol | 426.31 |
| 34 | 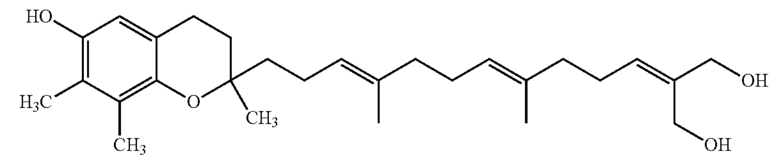 [SMILES: C/C(=C\CC/C(C)=C/CCC1(C)CCc2cc(O)c(C)c(C)c2O1)CCC=C(CO)CO] | 2-((4E,8E)-11-(6-hydroxy-2,7,8-trimethylchroman-2-yl)-4,8-dimethylundeca-4,8-dien-1-ylidene)propane-1,3-diol | 442.31 |
| 35 | 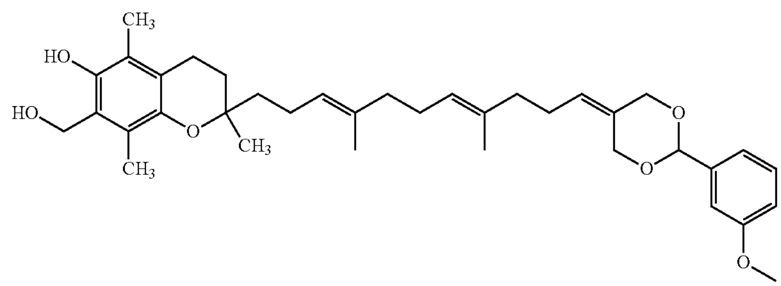 [SMILES: COc1cccc(C2OCC(=CCC/C(C)=C/CC/C(C)=C/CCC3(C)CCc4c(C)c(O)c(CO)c(C)c4O3)CO2)c1] | 7-(hydroxymethyl)-2-((3E,7E)-1-(2-(3-methoxyphenyl)-1,3-dioxan-5-ylidene)-4,8-dimethylundeca-3,7-dien-1-yl)-2,5,8-trimethylchroman-6-ol | 590.36 |
| 36 | 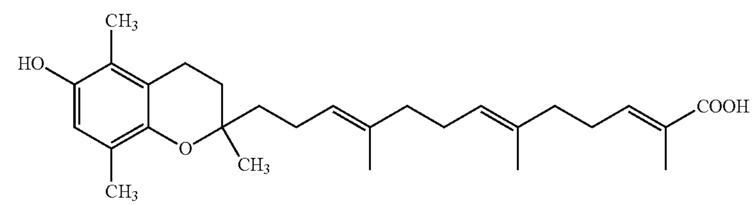 [SMILES: C/C(=C\CC/C(C)=C/CCC1(C)CCc2c(C)c(O)cc(C)c2O1)CC/C=C(\C)C(=O)O] | (2E,6E,10E)-13-(6-hydroxy-2,5,8-trimethylchroman-2-yl)-2,6,10-trimethyltrideca-2,6,10-trienoic acid | 440.29 |
| 37 | 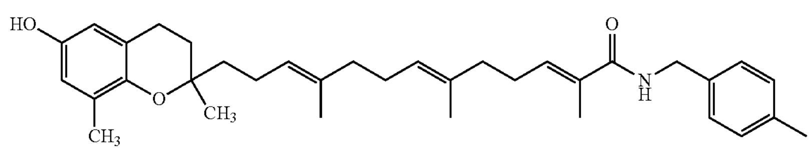 [SMILES: C/C(=C\CC/C(C)=C/CCC1(C)CCc2cc(O)cc(C)c2O1)CC/C=C(\C)C(=O)NCc1ccc(C)cc1] | (2E,6E,10E)-13-(6-hydroxy-2,8-dimethylchroman-2-yl)-2,6,10-trimethyl-N-(4-methylbenzyl)trideca-2,6,10-trienamide | 529.36 |
| 38 | 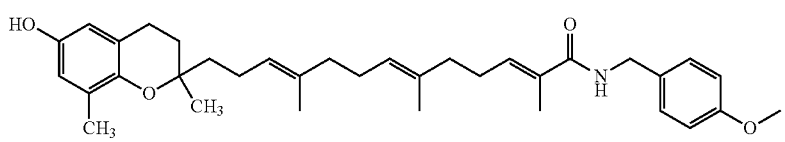 [SMILES: COc1ccc(CNC(=O)/C(C)=C/CC/C(C)=C/CC/C(C)=C/CCC2(C)CCc3cc(O)cc(C)c3O2)cc1] | (2E,6E,10E)-13-(6-hydroxy-2,8-dimethylchroman-2-yl)-N-(4-methoxybenzyl)-2,6,10-trimethyltrideca-2,6,10-trienamide | 545.35 |
| 39 | 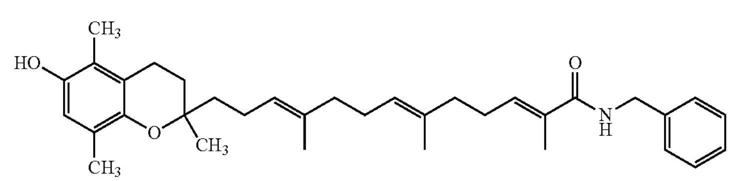 [SMILES: C/C(=C\CC/C(C)=C/CCC1(C)CCc2c(C)c(O)cc(C)c2O1)CC/C=C(\C)C(=O)NCc1ccccc1] | (2E,6E,10E)-N-benzyl-13-(6-hydroxy-2,5,8-trimethylchroman-2-yl)-2,6,10-trimethyltrideca-2,6,10-trienamide | 529.75 |
| 40 | 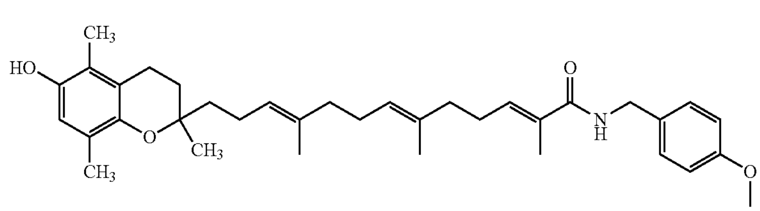 [SMILES: COc1ccc(CNC(=O)/C(C)=C/CC/C(C)=C/CC/C(C)=C/CCC2(C)CCc3c(C)c(O)cc(C)c3O2)cc1] | (2E,6E,10E)-13-(6-hydroxy-2,5,8-trimethylchroman-2-yl)-N-(4-methoxybenzyl)-2,6,10-trimethyltrideca-2,6,10-trienamide | 559.78 |

TABLE 1-continued

| Cpd n° | Structure | Chemical name | MW |
|---|---|---|---|
| 41 | 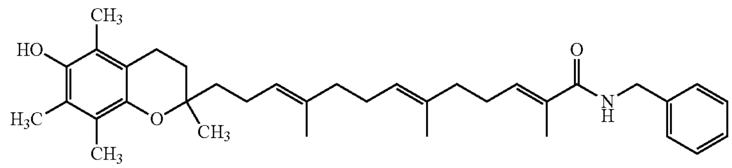 [SMILES: C/C(=C\CC/C(C)=C/CCC1(C)CCc2c(C)c(O)c(C)c(C)c2O1)CC/C=C(\C)C(=O)NCc1ccccc1] | (2E,6E,10E)-N-benzyl-13-(6-hydroxy-2,5,7,8-tetramethylchroman-2-yl)-2,6,10-trimethyltrideca-2,6,10-trienamide | 543.78 |
| 42 | 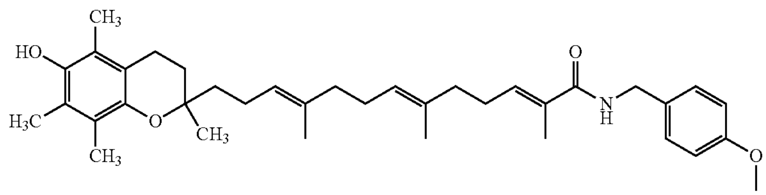 [SMILES: COc1ccc(CNC(=O)/C(C)=C/CC/C(C)=C/CC/C(C)=C/CCC2(C)CCc3c(C)c(O)c(C)c(C)c3O2)cc1] | (2E,6E,10E)-13-(6-hydroxy-2,5,7,8-tetramethylchroman-2-yl)-N-(4-methoxybenzyl)-2,6,10-trimethyltrideca-2,6,10-trienamide | 573.81 |
| 43 | 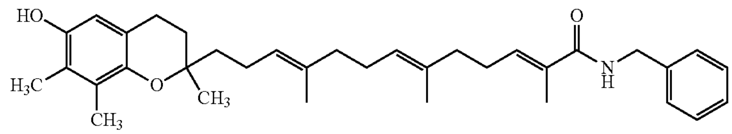 [SMILES: C/C(=C\CC/C(C)=C/CCC1(C)CCc2cc(O)c(C)c(C)c2O1)CC/C=C(\C)C(=O)NCc1ccccc1] | (2E,6E,10E)-N-benzyl-13-(6-hydroxy-2,7,8-trimethylchroman-2-yl)-2,6,10-trimethyltrideca-2,6,10-trienamide | 529.75 |
| 44 | 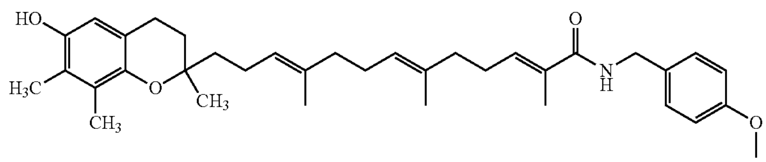 [SMILES: COc1ccc(CNC(=O)/C(C)=C/CC/C(C)=C/CC/C(C)=C/CCC2(C)CCc3cc(O)c(C)c(C)c3O2)cc1] | (2E,6E,10E)-13-(6-hydroxy-2,7,8-trimethylchroman-2-yl)-N-(4-methoxybenzyl)-2,6,10-trimethyltrideca-2,6,10-trienamide | 559.78 |
| 45 | 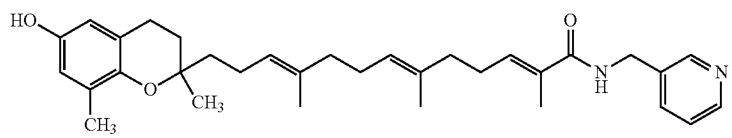 [SMILES: C/C(=C\CC/C(C)=C/CCC1(C)CCc2cc(O)cc(C)c2O1)CC/C=C(\C)C(=O)NCc1cccnc1] | (2E,6E,10E)-13-(6-hydroxy-2,8-dimethylchroman-2-yl)-2,6,10-trimethyl-N-(pyridin-3-ylmethyl)trideca-2,6,10-trienamide | 516.71 |
| 46 | 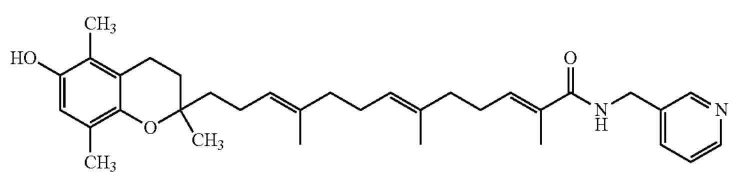 [SMILES: C/C(=C\CC/C(C)=C/CCC1(C)CCc2c(C)c(O)cc(C)c2O1)CC/C=C(\C)C(=O)NCc1cccnc1] | (2E,6E,10E)-13-(6-hydroxy-2,5,8-trimethylchroman-2-yl)-2,6,10-trimethyl-N-(pyridin-3-ylmethyl)trideca-2,6,10-trienamide | 530.74 |
| 47 | 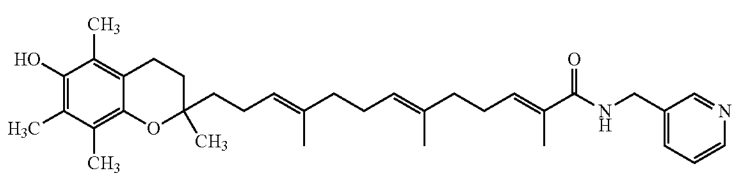 [SMILES: C/C(=C\CC/C(C)=C/CCC1(C)CCc2c(C)c(O)c(C)c(C)c2O1)CC/C=C(\C)C(=O)NCc1cccnc1] | (2E,6E,10E)-13-(6-hydroxy-2,5,7,8-tetramethylchroman-2-yl)-2,6,10-trimethyl-N-(pyridin-3-ylmethyl)trideca-2,6,10-trienamide | 544.77 |
| 48 | 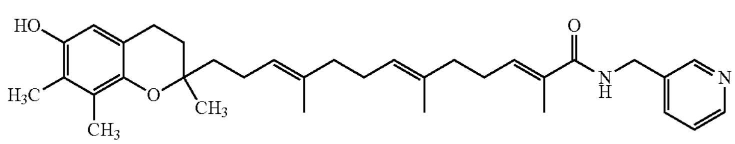 [SMILES: C/C(=C\CC/C(C)=C/CCC1(C)CCc2cc(O)c(C)c(C)c2O1)CC/C=C(\C)C(=O)NCc1cccnc1] | (2E,6E,10E)-13-(6-hydroxy-2,7,8-trimethylchroman-2-yl)-2,6,10-trimethyl-N-(pyridin-3-ylmethyl)trideca-2,6,10-trienamide | 530.74 |
| 49 | 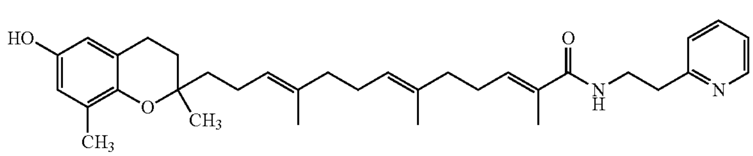 [SMILES: C/C(=C\CC/C(C)=C/CCC1(C)CCc2cc(O)cc(C)c2O1)CC/C=C(\C)C(=O)NCCc1ccccn1] | (2E,6E,10E)-13-(6-hydroxy-2,8-dimethylchroman-2-yl)-2,6,10-trimethyl-N-(2-(pyridin-2-yl)ethyl)trideca-2,6,10-trienamide | 530.74 |

TABLE 1-continued

| Cpd n° | Structure | Chemical name | MW |
|---|---|---|---|
| 50 | 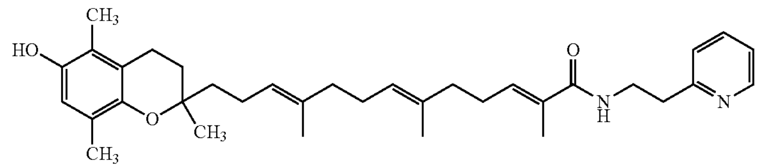 [SMILES: C/C(=C\CC/C(C)=C/CCC1(C)CCc2c(C)c(O)cc(C)c2O1)CC/C=C(\C)C(=O)NCCc1ccccn1] | (2E,6E,10E)-13-(6-hydroxy-2,5,8-trimethylchroman-2-yl)-2,6,10-trimethyl-N-(2-(pyridin-2-yl)ethyl)trideca-2,6,10-trienamide | 544.77 |
| 51 | 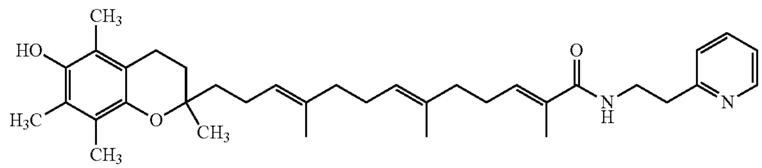 [SMILES: C/C(=C\CC/C(C)=C/CCC1(C)CCc2c(C)c(O)c(C)c(C)c2O1)CC/C=C(\C)C(=O)NCCc1ccccn1] | (2E,6E,10E)-13-(6-hydroxy-2,5,7,8-tetramethylchroman-2-yl)-2,6,10-trimethyl-N-(2-(pyridin-2-yl)ethyl)trideca-2,6,10-trienamide | 558.79 |
| 52 | 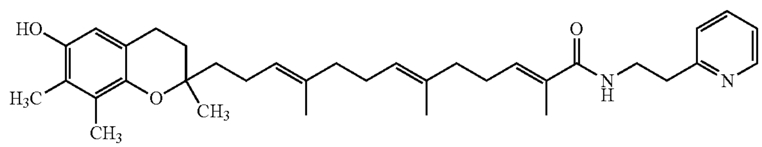 [SMILES: C/C(=C\CC/C(C)=C/CCC1(C)CCc2cc(O)c(C)c(C)c2O1)CC/C=C(\C)C(=O)NCCc1ccccn1] | (2E,6E,10E)-13-(6-hydroxy-2,7,8-trimethylchroman-2-yl)-2,6,10-trimethyl-N-(2-(pyridin-2-yl)ethyl)trideca-2,6,10-trienamide | 544.77 |
| 53 | 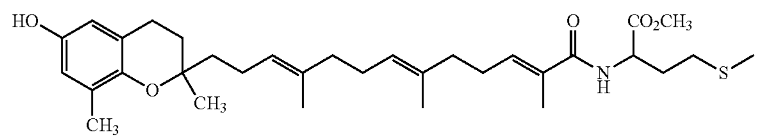 [SMILES: COC(=O)C(CCSC)NC(=O)/C(C)=C/CC/C(C)=C/CC/C(C)=C/CCC1(C)CCc2cc(O)cc(C)c2O1] | methyl 2-(((2E,6E,10E)-13-(6-hydroxy-2,8-dimethylchroman-2-yl)-2,6,10-trimethyltrideca-2,6,10-trienamido)-4-(methylthio)butanoate | 571.81 |
| 54 | 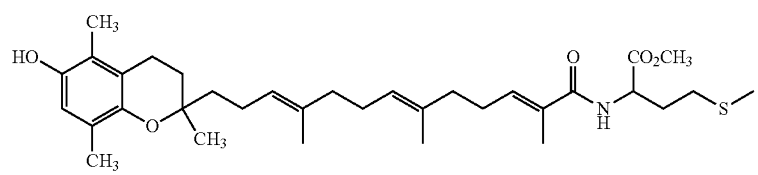 [SMILES: COC(=O)C(CCSC)NC(=O)/C(C)=C/CC/C(C)=C/CC/C(C)=C/CCC1(C)CCc2c(C)c(O)cc(C)c2O1] | methyl 2-(((2E,6E,10E)-13-(6-hydroxy-2,5,8-trimethylchroman-2-yl)-2,6,10-trimethyltrideca-2,6,10-trienamido)-4-(methylthio)butanoate | 585.84 |
| 55 | 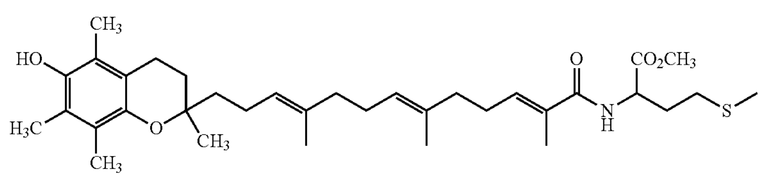 [SMILES: COC(=O)C(CCSC)NC(=O)/C(C)=C/CC/C(C)=C/CC/C(C)=C/CCC1(C)CCc2c(C)c(O)c(C)c(C)c2O1] | methyl 2-(((2E,6E,10E)-13-(6-hydroxy-2,5,7,8-tetramethylchroman-2-yl)-2,6,10-trimethyltrideca-2,6,10-trienamido)-4-(methylthio)butanoate | 599.86 |
| 56 | 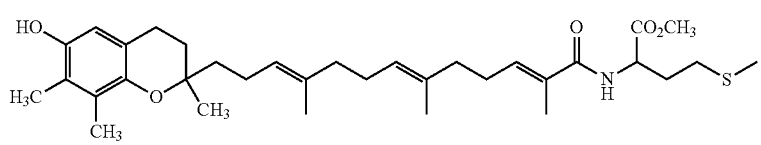 [SMILES: COC(=O)C(CCSC)NC(=O)/C(C)=C/CC/C(C)=C/CC/C(C)=C/CCC1(C)CCc2cc(O)c(C)c(C)c2O1] | methyl 2-(((2E,6E,10E)-13-(6-hydroxy-2,7,8-trimethylchroman-2-yl)-2,6,10-trimethyltrideca-2,6,10-trienamido)-4-(methylthio)butanoate | 585.84 |
| 57 | 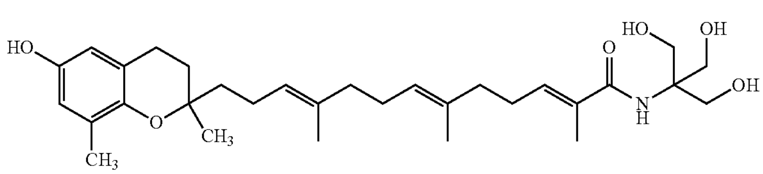 [SMILES: C/C(=C\CC/C(C)=C/CCC1(C)CCc2cc(O)cc(C)c2O1)CC/C=C(\C)C(=O)NC(CO)(CO)CO] | (2E,6E,10E)-N-(1,3-dihydroxy-2-(hydroxymethyl)propan-2-yl)-13-(6-hydroxy-2,8-dimethylchroman-2-yl)-2,6,10-trimethyltrideca-2,6,10-trienamide | 529.71 |

TABLE 1-continued

| Cpd n° | Structure | Chemical name | MW |
|---|---|---|---|
| 58 | 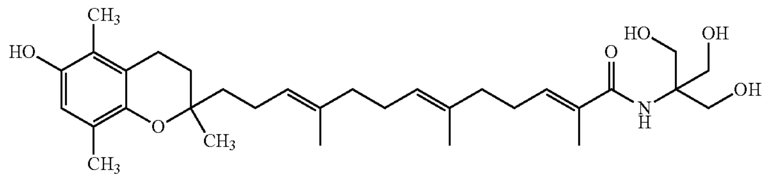 [SMILES: C/C(=C\CC/C(C)=C/CCC1(C)CCc2c(C)c(O)cc(C)c2O1)CC/C=C(\C)C(=O)NC(CO)(CO)CO] | (2E,6E,10E)-N-(1,3-dihydroxy-2-(hydroxymethyl)propan-2-yl)-13-(6-hydroxy-2,5,8-trimethylchroman-2-yl)-2,6,10-trimethyltrideca-2,6,10-trienamide | 543.73 |
| 59 | 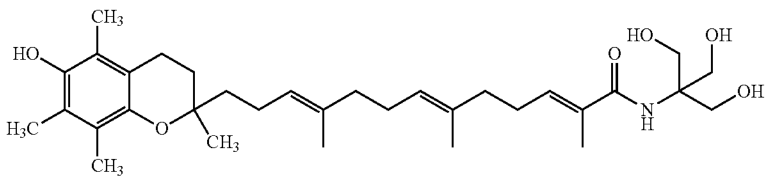 [SMILES: C/C(=C\CC/C(C)=C/CCC1(C)CCc2c(C)c(O)c(C)c(C)c2O1)CC/C=C(\C)C(=O)NC(CO)(CO)CO] | (2E,6E,10E)-N-(1,3-dihydroxy-2-(hydroxymethyl)propan-2-yl)-13-(6-hydroxy-2,5,7,8-tetramethylchroman-2-yl)-2,6,10-trimethyltrideca-2,6,10-trienamide | 557.76 |
| 60 | 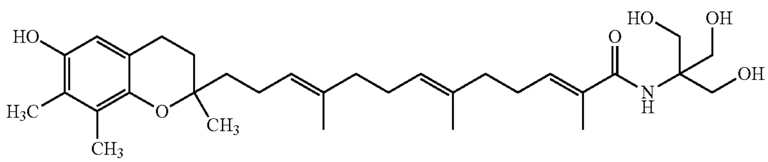 [SMILES: C/C(=C\CC/C(C)=C/CCC1(C)CCc2cc(O)c(C)c(C)c2O1)CC/C=C(\C)C(=O)NC(CO)(CO)CO] | (2E,6E,10E)-N-(1,3-dihydroxy-2-(hydroxymethyl)propan-2-yl)-13-(6-hydroxy-2,7,8-trimethylchroman-2-yl)-2,6,10-trimethyltrideca-2,6,10-trienamide | 543.73 |
| 61 | 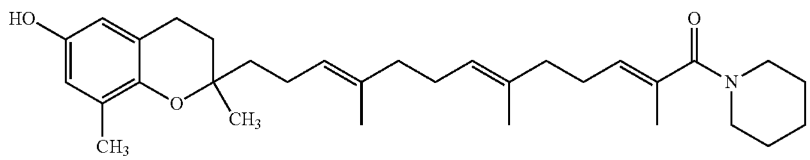 [SMILES: C/C(=C\CC/C(C)=C/CCC1(C)CCc2cc(O)cc(C)c2O1)CC/C=C(\C)C(=O)N1CCCCC1] | (2E,6E,10E)-13-(6-hydroxy-2,8-dimethylchroman-2-yl)-2,6,10-trimethyl-1-(piperidin-1-yl)trideca-2,6,10-trien-1-one | 493.72 |
| 62 | 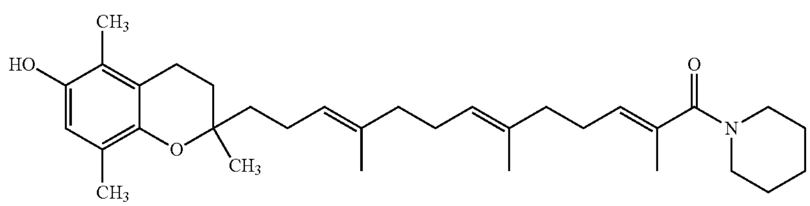 [SMILES: C/C(=C\CC/C(C)=C/CCC1(C)CCc2c(C)c(O)cc(C)c2O1)CC/C=C(\C)C(=O)N1CCCCC1] | (2E,6E,10E)-13-(6-hydroxy-2,5,8-trimethylchroman-2-yl)-2,6,10-trimethyl-1-(piperidin-1-yl)trideca-2,6,10-trien-1-one | 507.75 |
| 63 | 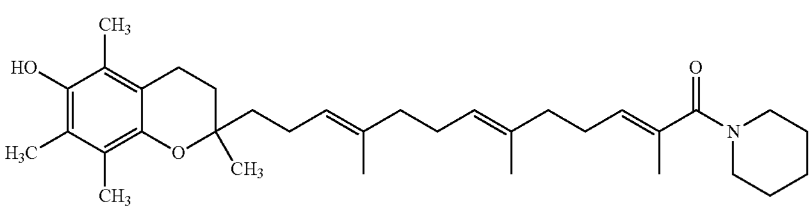 [SMILES: C/C(=C\CC/C(C)=C/CCC1(C)CCc2c(C)c(O)c(C)c(C)c2O1)CC/C=C(\C)C(=O)N1CCCCC1] | (2E,6E,10E)-13-(6-hydroxy-2,5,7,8-tetramethylchroman-2-yl)-2,6,10-trimethyl-1-(piperidin-1-yl)trideca-2,6,10-trien-1-one | 521.77 |
| 64 | 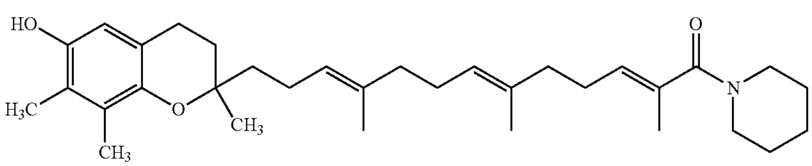 [SMILES: C/C(=C\CC/C(C)=C/CCC1(C)CCc2cc(O)c(C)c(C)c2O1)CC/C=C(\C)C(=O)N1CCCCC1] | (2E,6E,10E)-13-(6-hydroxy-2,7,8-trimethylchroman-2-yl)-2,6,10-trimethyl-1-(piperidin-1-yl)trideca-2,6,10-trien-1-one | 507.75 |
| 65 | 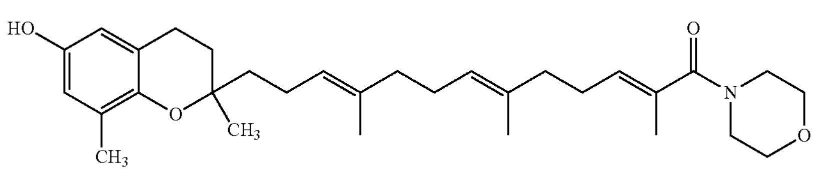 [SMILES: C/C(=C\CC/C(C)=C/CCC1(C)CCc2cc(O)cc(C)c2O1)CC/C=C(\C)C(=O)N1CCOCC1] | (2E,6E,10E)-13-(6-hydroxy-2,8-dimethylchroman-2-yl)-2,6,10-trimethyl-1-morpholinotrideca-2,6,10-trien-1-one | 495.69 |

TABLE 1-continued

| Cpd n° | Structure | Chemical name | MW |
|---|---|---|---|
| 66 | 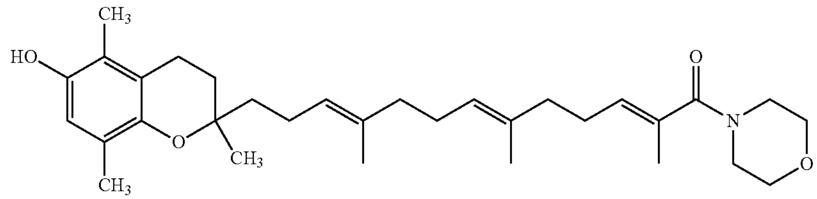 [SMILES: C/C(=C\CC/C(C)=C/CCC1(C)CCc2c(C)c(O)cc(C)c2O1)CC/C=C(\C)C(=O)N1CCOCC1] | (2E,6E,10E)-13-(6-hydroxy-2,5,8-trimethylchroman-2-yl)-2,6,10-trimethyl-1-morpholinotrideca-2,6,10-trien-1-one | 509.72 |
| 67 | 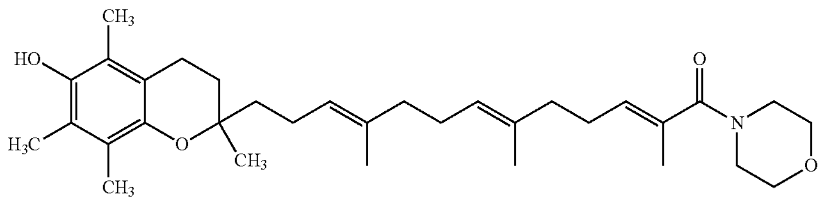 [SMILES: C/C(=C\CC/C(C)=C/CCC1(C)CCc2c(C)c(O)c(C)c(C)c2O1)CC/C=C(\C)C(=O)N1CCOCC1] | (2E,6E,10E)-13-(6-hydroxy-2,5,7,8-tetramethylchroman-2-yl)-2,6,10-trimethyl-1-morpholinotrideca-2,6,10-trien-1-one | 523.75 |
| 68 | 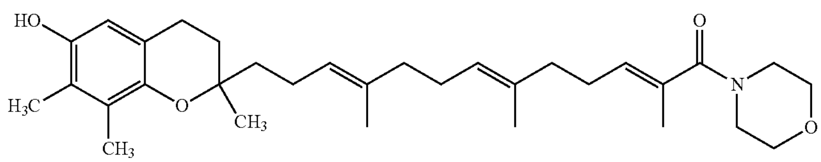 [SMILES: C/C(=C\CC/C(C)=C/CCC1(C)CCc2cc(O)c(C)c(C)c2O1)CC/C=C(\C)C(=O)N1CCOCC1] | (2E,6E,10E)-13-(6-hydroxy-2,7,8-trimethylchroman-2-yl)-2,6,10-trimethyl-1-morpholinotrideca-2,6,10-trien-1-one | 509.72 |
| 69 | 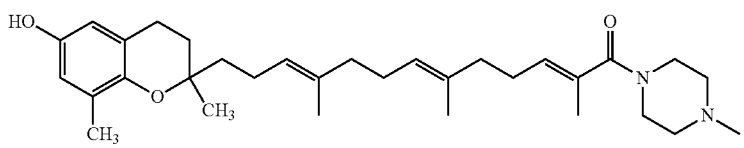 [SMILES: C/C(=C\CC/C(C)=C/CCC1(C)CCc2cc(O)cc(C)c2O1)CC/C=C(\C)C(=O)N1CCN(C)CC1] | (2E,6E,10E)-13-(6-hydroxy-2,8-dimethylchroman-2-yl)-2,6,10-trimethyl-1-(4-methylpiperazin-1-yl)trideca-2,6,10-trien-1-one | 508.74 |
| 70 | 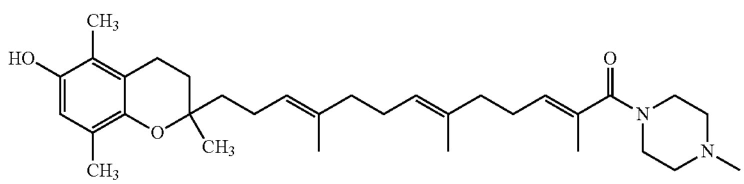 [SMILES: C/C(=C\CC/C(C)=C/CCC1(C)CCc2c(C)c(O)cc(C)c2O1)CC/C=C(\C)C(=O)N1CCN(C)CC1] | (2E,6E,10E)-13-(6-hydroxy-2,5,8-trimethylchroman-2-yl)-2,6,10-trimethyl-1-(4-methylpiperazin-1-yl)trideca-2,6,10-trien-1-one | 522.76 |
| 71 | 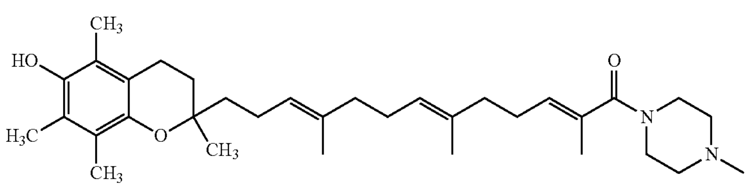 [SMILES: C/C(=C\CC/C(C)=C/CCC1(C)CCc2c(C)c(O)c(C)c(C)c2O1)CC/C=C(\C)C(=O)N1CCN(C)CC1] | (2E,6E,10E)-13-(6-hydroxy-2,5,7,8-tetramethylchroman-2-yl)-2,6,10-trimethyl-1-(4-methylpiperazin-1-yl)trideca-2,6,10-trien-1-one | 536.79 |
| 72 | | (2E,6E,10E)-13-(6-hydroxy-2,7,8-trimethylchroman-2-yl)-2,6,10-trimethyl-1-(4-methylpiperazin-1-yl)trideca-2,6,10-trien-1-one | 522.76 | and pharmaceutically acceptable solvates thereof.

In Table 1, the term "Cpd" means compound.

The compounds of Table 1 were named using ChemBioDraw® Ultra version 12.0 (PerkinElmer).

Preferred compounds of the present invention are compounds 1, 2, 9, 11, 26, 32 and 34; preferably, compounds 1, 9 and 34; more preferably compounds 1 and 9.

According to one embodiment, preferred compounds of the invention are compounds 10, 25, 29, 30, 35 and 36.

The present invention also refers to compounds of formula (I) provided that $R_2$ does not represent H.

The present invention also refers to compounds of formula (I) provided that the $IC_{50}$ of said compounds on the 5-LO activity is less than 350 nM; preferably, less than 150 nM and/or provided that the $IC_{50}$ of said compounds on the neutrophil 5-LO product formation is less than 600 nM; preferably, less than 300 nM.

The $IC_{50}$ was measured by a method well-known by the skilled artisan.

Extract

The present invention also refers to a plant extract comprising at least one tocotrienol derivative of the invention. Especially, the plant extract of the present invention is rich in tocotrienols. In one embodiment, a plant extract rich in tocotrienol comprises at least one tocotrienol of formula (I) and a total concentration in tocotrienols higher than 0.1% in weight of the total weight of plant extract; preferably; higher than 1%; more preferably ranging from 1 to 30%. In one embodiment, the total concentration in tocotrienols is the total concentration of all tocotrienols in the plant extract, whether tocotrienols of formula (I) of the invention or others tocotrienols.

In one embodiment, the plant extract of the invention is a dry extract.

In one embodiment, the plant extract of the invention is obtained with an extraction yield ranging from 1% to 60% by weight to the total weight of dry matter. In one embodiment, the extraction is realized in presence of dichloromethane and the extraction yield is ranging from 1% to 25%; preferably from 5 to 20% in weight to the total weight of the dry extract. In one embodiment, the extraction is realized in presence of ethanol and the extraction yield is ranging from 20% to 56%; preferably from 30 to 50% in weight to the total weight of the dry extract.

In one embodiment, the plant extract of the invention is achieved by extraction of dried leaves and/or dried bark and/or dried fruits and/or of latex of species of the Clusiaceae family In one embodiment, the plant extract of the invention is achieved by extraction of dried leaves and/or dried bark and/or dried fruits and/or of latex of *Garcinia kola*. In one embodiment, the plant extract of the invention is achieved by extraction of dried leaves and/or dried bark and/or dried fruits and/or of latex of *Garcinia amplexicaulis*.

In one embodiment, the extraction is implemented in presence of a solvent selected from the group comprising alkanes, such as for example, hexane; halogenated alkanes, such as chloroform or dichloromethane for example; ethers, such as diethyl ether for example; esters, such as ethyl acetate for example; alcohols, such as ethanol; or any mixture of these solvents; preferably ethanol or dichloromethane.

In one embodiment, the grade of *Garcinia kola* or *Garcinia amplexicaulis* dry extract of the present invention ranges from 5 to 100 mg; preferably from 10 to 60 mg; more preferably from 15 to 47 mg in compounds of formula (I) for 1 g of dried extracts of *Garcinia kola* or *Garcinia amplexicaulis*. In one embodiment, compounds of formula (I) are extracts from bark of *Garcinia amplexicaulis*. In one embodiment, compounds of formula (I) are extracts from nuts of *Garcinia kola*. In one embodiment, the grade of *Garcinia kola* or *Garcinia amplexicaulis* dry extract obtained by the process of the invention ranges from 1 to 10 mg; preferably from 3 to 4 mg in compounds of formula (I) for 1 g of dried bark of *Garcinia kola* or *Garcinia amplexicaulis*.

In one embodiment, the grade of *Garcinia kola* or *Garcinia amplexicaulis* dry extract of the present invention ranges from 0.5 mg to 20 mg; preferably from 1 to 10 mg; more preferably from 2 to 8 mg in compounds of formula (I) for 1 g of dried bark of *Garcinia koa* or *Garcinia amplexicaulis*. In one embodiment, the grade of *Garcinia kola* or *Garcinia amplexicaulis* dry extract obtained by the process of the invention ranges from 0.01 mg to 5 mg; preferably from 0.05 to 1 mg; more preferably from 0.1 to 0.5 mg in compounds of formula (I) for 1 g of dried bark of *Garcinia kola* or *Garcinia amplexicaulis*.

Process for Preparing Compounds of the Invention

The compounds of the invention can be prepared by different ways with reactions.

The invention further relates to a process of manufacturing of compounds of formula (I) as defined above.

According to one embodiment, the present invention relates to the process of extracting compounds of the invention from a plant.

In one embodiment, the process of invention comprises at least one extraction step from a vegetal source in presence of a solvent and leading to an extract of the invention; preferably a plant extract rich in tocotrienol derivatives from the invention.

In one embodiment, the vegetal source belongs to the Clusiaceae family; preferably to *Garcinia*. In one embodiment, the vegetal source is *Garcinia kola*. In one embodiment, the vegetal source is *Garcinia amplexicaulis*.

According to another embodiment, the present invention relates to a process for preparing compounds of the invention by semi-synthesis comprising at least one extraction step of a delta or a gamma tocotrienol derivative of formula (I).

The present invention also refers to a composition, a pharmaceutical composition or a medicament comprising the compositions of the invention as defined above.

The compounds of the invention are therefore useful as medicaments, in particular in the prevention and/or treatment of 5-LO-mediated diseases.

The compounds of the invention are therefore useful as medicaments, in particular in the prevention and/or treatment of chronic airway inflammatory diseases such as, but not limited to, asthma, chronic obstructive pulmonary disease (COPD), aspirin-induced asthma, allergic rhinitis, sinusitis, chronic bronchitis or anaphylaxis.

The compounds of the invention are therefore useful as medicaments, in particular in the prevention and/or treatment of inflammatory skin diseases such as, but not limited to, atopic dermatitis.

Preferably, the patient is a warm-blooded animal, more preferably a human.

In a specific embodiment, the compounds of the invention are especially useful in the treatment and/or prevention of asthma.

Uses

The invention further provides the use of compounds of the invention or a pharmaceutically acceptable solvate thereof for the manufacture of a medicament; especially, for treating and/or preventing 5-LO-mediated diseases. In one embodiment, the invention refers to the use of compounds of formula (I) or of formula (I') of the invention or a pharmaceutically acceptable solvate thereof for the manufacture of a medicament for treating and/or preventing 5-LO-mediated diseases. In one embodiment, the invention refers to the use of compounds of formula (II) of the invention or a pharmaceutically acceptable solvate thereof for the manufacture of a medicament for treating and/or preventing 5-LO-mediated diseases. In one embodiment, the invention refers to the use of compounds of formula (III) of the invention or a pharmaceutically acceptable solvate thereof for the manufacture of a medicament for treating and/or preventing 5-LO-mediated diseases. In one embodiment, the invention refers to the use of compounds of formula (IV) of the invention or a pharmaceutically acceptable solvate thereof for the manufacture of a medicament for treating and/or preventing 5-LO-mediated diseases. In one embodiment, the invention refers to the use of compounds of formula (V) of the invention or a pharmaceutically acceptable solvate thereof for the manufacture of a medicament for treating and/or preventing 5-LO-mediated diseases.

The invention further provides the use of compounds of the invention or a pharmaceutically acceptable solvate thereof for the manufacture of a medicament for treating and/or preventing inflammatory skin diseases, inflammatory bowel diseases such as ulcerative colitis or Crohn's disease, cardiovascular diseases such as atherosclerotic disease, gastroesophageal reflux diseases or chronic airway inflammatory diseases such as, but not limited to, asthma, chronic obstructive pulmonary disease (COPD), aspirin-induced asthma, allergic rhinitis, sinusitis, chronic bronchitis or anaphylaxis.

In one embodiment, the invention refers to the use of compounds of formula (I) or of formula (I') or a pharmaceutically acceptable solvate thereof for the manufacture of a medicament for treating and/or preventing inflammatory skin diseases, inflammatory bowel diseases such as ulcerative colitis or Crohn's disease, cardiovascular diseases such as atherosclerotic disease, gastroesophageal reflux diseases or chronic airway inflammatory diseases such as, but not limited to, asthma, chronic obstructive pulmonary disease (COPD) such as idiopathic pulmonary fibrosis, aspirin-induced asthma, allergic diseases such as allergic rhinitis, sinusitis, chronic bronchitis or anaphylaxis. In one embodiment, the invention refers to the use of compounds of formula (II) or a pharmaceutically acceptable solvate thereof for the manufacture of a medicament for treating and/or preventing inflammatory skin diseases, inflammatory bowel diseases such as ulcerative colitis or Crohn's disease, cardiovascular diseases such as atherosclerotic disease, gastroesophageal reflux diseases or chronic airway inflammatory diseases such as, but not limited to, asthma, chronic obstructive pulmonary disease (COPD) such as idiopathic pulmonary fibrosis, aspirin-induced asthma, allergic diseases such as allergic rhinitis, sinusitis, chronic bronchitis or anaphylaxis. In one embodiment, the invention refers to the use of compounds of formula (III) or a pharmaceutically acceptable solvate thereof for the manufacture of a medicament for treating and/or preventing inflammatory skin diseases, inflammatory bowel diseases such as ulcerative colitis or Crohn's disease, cardiovascular diseases such as atherosclerotic disease, gastroesophageal reflux diseases or chronic airway inflammatory diseases such as, but not limited to, asthma, chronic obstructive pulmonary disease (COPD), aspirin-induced asthma, allergic rhinitis, sinusitis, chronic bronchitis or anaphylaxis. In one embodiment, the invention refers to the use of compounds of formula (IV) or a pharmaceutically acceptable solvate thereof for the manufacture of a medicament for treating and/or preventing inflammatory skin diseases, inflammatory bowel diseases such as ulcerative colitis or Crohn's disease, cardiovascular diseases such as atherosclerotic disease, gastroesophageal reflux diseases or chronic airway inflammatory diseases such as, but not limited to, asthma, chronic obstructive pulmonary disease (COPD), aspirin-induced asthma, allergic rhinitis, sinusitis, chronic bronchitis or anaphylaxis. In one embodiment, the invention refers to the use of compounds of formula (V) or a pharmaceutically acceptable solvate thereof for the manufacture of a medicament for treating and/or preventing inflammatory skin diseases, inflammatory bowel diseases such as ulcerative colitis or Crohn's disease, cardiovascular diseases such as atherosclerotic disease, gastroesophageal reflux diseases or chronic airway inflammatory diseases such as, but not limited to, asthma, chronic obstructive pulmonary disease (COPD), aspirin-induced asthma, allergic rhinitis, sinusitis, chronic bronchitis or anaphylaxis.

According to one embodiment, the invention refers to compounds of the invention for use as a medicament.

According to one embodiment, the invention refers to compounds of the invention for use in the treatment and/or prevention of inflammatory skin diseases, inflammatory bowel diseases such as ulcerative colitis or Crohn's disease, cardiovascular diseases such as atherosclerotic disease, gastroesophageal reflux diseases chronic airway inflammatory diseases.

According to one embodiment, the invention refers to compounds of the invention for use in the treatment and/or prevention of dermatological diseases.

In one embodiment, the dermatological disease is selected from acne, alopecia areata, basal cell carcinoma, Bowen's disease, erythropoietic porphyria, dermatitis, Darier's disease, dystrophic epidermolysis bullosa, eczema, epidermolysis bullocsa simplex, erythropoietic protoporphyria, fungal infections of nails, Hailey-Hailey disease, herpes simplex, hidradenitis suppurativa, hirsutism, hyperhidrosis, ichthyosis, impetigo, keloids, keratosis pilaris, lichen planus, lichen sclerosus, melanoma, melisma, pemphigus vulgaris, plantar warts (verrucas), pityriasis lichenoides, polymorphic light eruption, psoriasis, pyoderma gangrenosum, rosacea, scabies, shingles, squamous cell carcinoma, Sweet's syndrome and vitiligo. In one embodiment, the dermatological disease is dermatitis, preferably, atopic dermatitis.

Advantageously, the compounds of the invention allow decreasing the release of the pro-inflammatory cytokines.

Advantageously, the compounds of the invention are potent inhibitor of 5-LO product formation in neutrophils; especially, the compounds of the invention are potent inhibitor both of the human recombinant 5-LO and of 5-LO product formation in neutrophils.

According to a further feature of the present invention there is a method provided for modulating 5-LO activity, in a patient, preferably a warm blooded animal, and even more preferably a human, in need of such treatment, which comprises administering to said patient an effective amount of compound of the present invention, or a pharmaceutically acceptable solvate thereof.

According to a further feature of the present invention there is a method provided for modulating 5-LO product formation (i.e. leukotriene formation), in a patient, preferably a warm blooded animal, and even more preferably a human, in need of such treatment, which comprises administering to said patient an effective amount of compound of the present invention, or a pharmaceutically acceptable solvate thereof.

According to one embodiment, the compounds of the invention and their pharmaceutically acceptable salts and/or solvates, respectively, may be administered as part of a combination therapy. Thus, are included within the scope of the present invention embodiments comprising coadministration of, and compositions and medicaments which contain, in addition to a compound of the present invention, a pharmaceutically acceptable solvate thereof as active ingredient, additional therapeutic agents and/or active ingredients. Such multiple drug regimens, often referred to as "combination therapy", may be used in the treatment and/or prevention of any of the diseases or conditions mediated by or associated with 5-LO activity modulation and/or associated with 5-LO product formation modulation. The use of such combinations of therapeutic agents is especially pertinent with respect to the treatment of the above-mentioned disorders within a patient in need of treatment or one at risk of becoming such a patient.

In addition to the requirement of therapeutic efficacy, which may necessitate the use of active agents in addition to the 5-LO product formation inhibitor compounds of the invention or pharmaceutical acceptable solvates thereof, there may be additional rationales which compel or highly recommend the use of combinations of drugs involving active ingredients which represent adjunct therapy, i.e., which complement and supplement the function performed by the 5-LO product formation inhibitor compounds of the present invention. Suitable supplementary therapeutic agents used for the purpose of auxiliary treatment include drugs which, instead of directly treating or preventing a disease or condition mediated by or associated with 5-LO product formation modulation, treat diseases or conditions which directly result from or indirectly accompany the basic or underlying 5-LO mediated disease or condition.

Thus, the methods of treatment and pharmaceutical compositions of the present invention may employ the compounds of invention or pharmaceutical acceptable solvates thereof in the form of monotherapy, but said methods and compositions may also be used in the form of multiple therapy in which one or more compounds of the invention or their pharmaceutically acceptable solvates are coadministered in combination with one or more other therapeutic agents.

In the above-described embodiment combinations of the present invention, the compounds of invention, pharmaceutically acceptable solvates thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The invention also provides pharmaceutical compositions comprising a compound of invention or a pharmaceutically acceptable solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable solvate thereof as active ingredient, additional therapeutic agents and/or active ingredients.

Another object of this invention is a medicament comprising at least one compound of the invention, or a pharmaceutically acceptable solvate thereof, as active ingredient.

According to a further feature of the present invention there is provided the use of a compound of the invention or a pharmaceutically acceptable solvate thereof for the manufacture of a medicament for inhibiting 5-LO activity and/or 5-LO product formation in a patient, in need of such treatment, which comprises administering to said patient an effective amount of compound of the present invention, or a pharmaceutically acceptable solvate thereof.

In one embodiment, the compound of the invention as defined above, inhibits from more than 0% to 100% of the 5-LO activity; preferably from 50% to 100%; even more preferably from 80% to 100% of the 5-LO activity. In one embodiment, the compound of the invention as defined above, totally inhibits the 5-LO activity. Methods for measuring the 5-LO activity are well-known from the skilled artisan. An example of such a method is disclosed in the Examples. Briefly, said method includes incubating human recombinant 5-LO with the tested compounds, expressing the 5-LO metabolites (all-trans isomers of LTB4 and 5-H(P)ETE) and measuring said metabolites by Reverse Phase-High Performance Liquid Chromatography (RP-HPLC) as described (Koeberle: Biochem. Pharmacol. 2009, 77, 1513-1521).

Preferably, the patient is a warm-blooded animal, more preferably a human.

As set forth above, the compounds of the invention or their pharmaceutically acceptable solvates may be used in monotherapy or in combination therapy. Thus, according to one embodiment, the invention provides the use of a compound of the invention for the manufacture of a medicament for at least one of the purposes described above, wherein said medicament is administered to a patient in need thereof, preferably a warm-blooded animal, and even more preferably a human, in combination with at least one additional therapeutic agent and/or active ingredient. The benefits and advantages of such a multiple drug regimen, possible administration regimens as well as suitable additional therapeutic agents and/or active ingredients are those described above.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, preferably between 2 and 150 mg of at least one compound of the invention, e.g. about 2, 4, 8, 16, 32, 64 or 128 mg per unit dosage.

Usually, depending on the condition to be prevented or treated and the route of administration, the active compound of the invention will usually be administered between 0.001 to 10 mg per kilogram body weight, more often between 0.01 and 4 mg per kilogram body weight, preferably between 0.02 and 1.5 mg per kilogram body weight, for example about 0.02, 0.04, 0.08, 0.16, 0.32, 0.64 or 1.28 mg per kilogram body weight of the patient per day, which may be administered as a single daily dose, divided over one or more daily doses, or essentially continuously, e.g. using a drip infusion.

According to one embodiment, the efficient concentration of the tocotrienol derivative of the invention ranges from more than 0 to 100 μM; preferably, from 0.01 to 90 μM; more preferably, from 0.1 to 50 μM; more preferably, from 0.1 to 20 μM. In one embodiment, the efficient concentration of the tocotrienol derivative of the invention ranges from 0.1 to 10 μM.

According to one embodiment, the tocotrienol derivatives of the invention are not toxic compounds. In one embodiment, the tocotrienol derivatives of the invention do not induce any toxicity on the liver.

EXAMPLES

Figure 1:
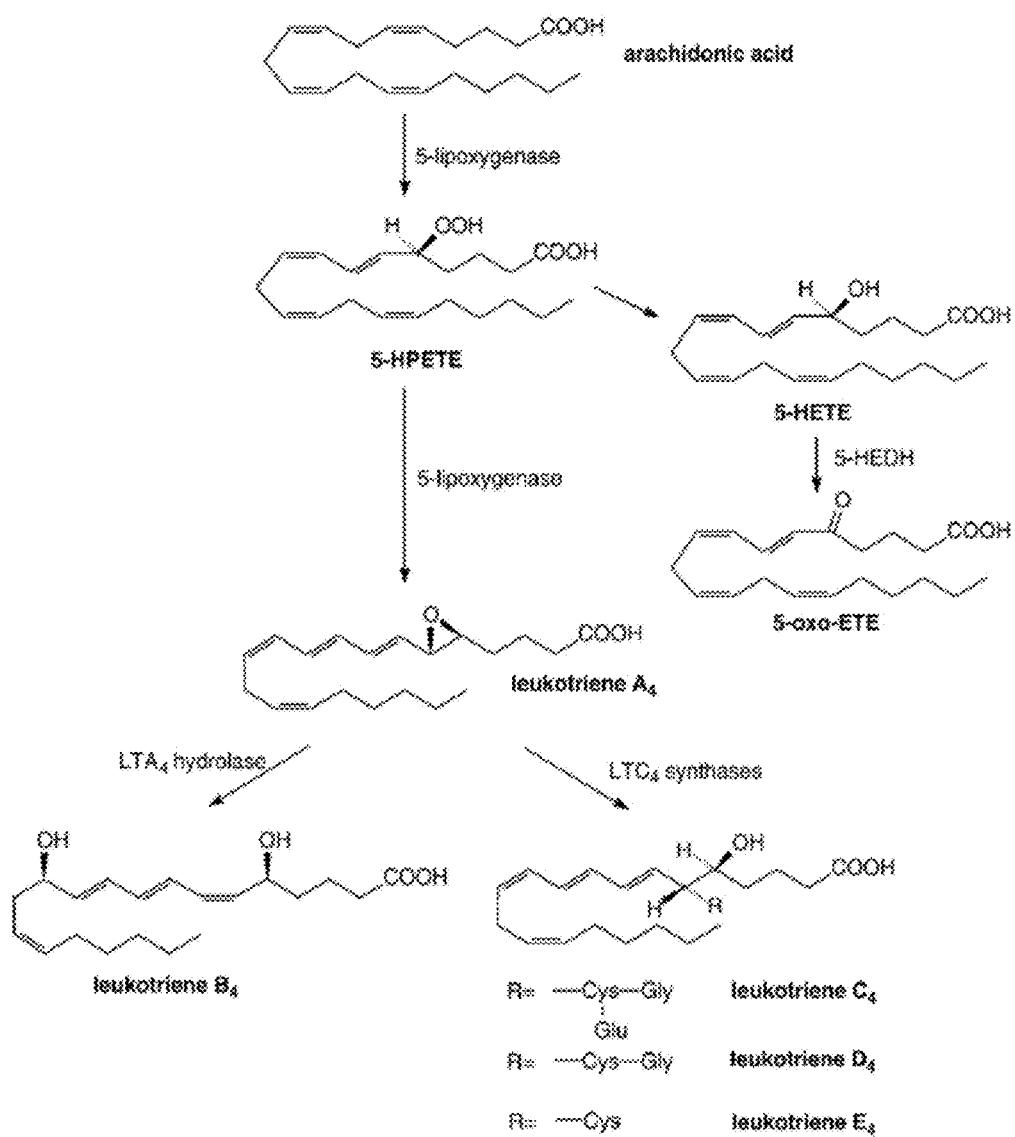
FIG. 1 is a scheme showing the 5-LO pathway, from Werz and Steinhilber, 2006.

The present invention will be better understood with reference to the following examples. These examples are intended to representative of specific embodiments of the invention, and are not intended as limiting the scope of the invention.

Material and Methods
General Experimental Procedures

Optical rotations were recorded on a P-2000 digital polarimeter (Jasco, Great Dunmow, UK). UV spectra were recorded on a Varian Cary 50 Bio spectrophotometer (Varian France, Les Ulis, France). $^1$H and $^{13}$C NMR along with 2D NMR data were obtained on a Bruker Avance DRX 500 MHz (500 and 125 MHz, respectively) spectrometer in CDCl$_3$ or CD$_3$COCD$_3$ with TMS as internal standard. Mass spectrometry analyses were performed on a JMS-700 (JEOL LTD, Akishima, Tokyo, Japan) double focusing mass spectrometer with reversed geometry, with EI or FAB as ionization sources. Chromatographic separations such as flash chromatography with an IntelliFlash 310 (Analogix, Burlington, USA) using a prepacked C18 (Interchim, Montlucon, France) or silica gel Chromabond flash RS column (Macherey-Nagel, Duren, Germany), and also preparative chromatography with a Varian ProStar 210 and a PrepStar 218 solvent delivery module (Agilent, Santa Clara, Calif., USA) with a C18 Varian column (5 pm; 250×21.4 mm) were used to purify the compounds.

Microwave irradiation experiments were carried out in a monowave 300 (Anton Paar, Graz, Austria). The reactions were carried out in 4 mL, 10 mL or 30 mL glass tubes, sealed with a Teflon septum. The temperature of the reactions in the microwave experiments was measured by an built-in infrared temperature probe.

Plant Material

The stem bark from *Garcinia amplexicaulis* was collected in July 1998 in the "Foret Cachée" area of southern New Caledonia. A specimen (LIT-0554) was deposited at the Laboratoire des Plantes Médicinales (CNRS), Noumea, New Caledonia (French sui generis Collectivity).

ABBREVIATIONS

BWA4C: N-RE)-3-(3-phenoxyphenye-prop-2-enyllacetohydroxamic acid;
Cpd: Compound;
DCM: Dichloromethane;
FAB-MS: Fast Atom Bombardment Mass Spectrometry;
eq.: Equivalent(s);
g: Gram(s);
h: Hour(s);
i.p.: intraperitoneal;
HREIMS: High Resolution Electron Impact Mass Spectrometry;
L: Liter(s);
LPS: lipopolysaccharide;
MeOH: Methanol;
MHz: Mega Hertz;
NaBH$_3$CN: Sodium cyanoborohydride;
NaHCO$_3$: Sodium hydrogen carbonate;
Na$_3$PO$_4$: Trisodium phosphate;
Na$_2$SO$_4$: Sodium sulfate;
mg: Milligram(s);
mL: Milliliter(s);
mmol: Millimole(s);
min: Minute(s);
TMS: trimethylsilane.

CHEMISTRY EXAMPLES

Extraction and Isolation of δ-amplexichromanol (Compound 26, Isomer R), δ-(Z)-deoxyamplexichromanol (Compound 23, Isomer R) and γ-garcinoic Acid (Compound 32, Isomer R):

The extraction and isolation of isomers R of compounds 23, 26 and 32 are described in: "Antiangiogenic tocotrienol derivatives from *Garcinia amplexicaulis*" Lavaud, Alexis; Richomme, Pascal; Litaudon, Marc; Andriantsitohaina, Ramaroson; Guilet, David J. Nat. Prod. (2013), 76(12), 2246-2252. DOI: 10.1021/np400598y and "A new biphenyl from *Clusia melchiorii* and a new tocotrienol from *C. obdeltifolia*" Teixeira, Josanaide S. R.; Moreira, Luciana de M.; Guedes, Maria L. da S.; Cruz, Frederico G., J. Braz. Chem. Soc. (2006), 17(4), 812-815. DOI:10.1590/50103-50532006000400027.

Briefly, dried *Garcinia amplexicaulis* stem bark (270 g) were extracted with 3 L of DCM using a Soxhlet apparatus for 24 h. The solvent was removed under reduced pressure to yield 29.7 g of extract. The DCM extract (20 g) was flash chromatographed on a 400 g silica gel column and eluted using as the mobile phase a mixture of three solvents A/B/C (A : DCM, B : DCM/acetone 90:10, C : acetone), at a constant flow rate of 70 mL/min as follow : 100:0:0 for 9 min, 100:0:0 to 50:50:0 for 21 min, 50:50:0 for 16 min, 50:50:0 to 0:100:0 for 22 min, 0:100:0 for 5 min, 90:0:10 to 80:0:20 for 15 min, 80:0:20 for 6 min, 80:0:20 to 50:0:50 for 24 min. This chromatography yielded 36 fractions (F1 to F36 in elution order), and F31, F32 and F33 were combined and afforded 4.5 g after solvent evaporation. The combined F31-33 were subjected to a reverse flash chromatography (puriflash PF-50C18/150 g Interchim) using water/methanol (50:50 to 35:65 for 30 min, 35:65 for 10 min, 35:65 to 15:85 for 40 min, 15:85 for 10 min, 15:85 to 10:90 for 10 min, 10:90 for 20 min, 20 mL/min) to obtain δ-amplexichromanol (compound 26, 3.1 g). Fraction F21 (290 mg) was purified by normal-phase vacuum flash chromatography using a cyclohexane/EtOAc mixture (95:5 to 1:1) to yield pure δ-(Z)-deoxyamplexichromanol (compound 23, 61.0 mg). Fraction F23 (300 mg) was separated by normal-phase flash chromatography with a cyclohexane/EtOAc mixture (9:1 to 1:1) to give 9 subfractions (F23-1 to F23-9).

Subfractions F23-7 to F23-9 were gathered and flash chromatographied over a RP-18 (4 g column, MeOH/H$_2$O mixture) to give pure γ-garcinoic acid (compound 32, 6.0 mg).

δ-(Z)-deoxyamplexichromanol (compound 23): pale yellow oil; [α]$^{22}_D$-17.7° (c 0.13, MeOH); UV (MeOH) λ$_{max}$ (log ε) 296.9 (3.53), 259.1 (2.68), 206.0 (4.58) nm; $^1$H NMR (CDCl$_3$, 500 MHz), δ$_H$: 1.26 (s, 3H, H-25), 1.53-1.66 (m, 2H, H-9), 1.57 (s, 3H, H-23), 1.58 (s, 3H, H-24), 1.75-1.83 (m, 2H, H-3), 1.78 (s, 3H, H-21), 1.97-2.06 (m, 2H, H-14), 1.98 (m, 2H, H-13), 1.98-2.09 (m, 2H, H-17), 2.06-2.11 (m, 2H, H-18), 2.10 (m, 2H, H-10), 2.12 (s, 3H, H-26), 2.69 (t (6.7 Hz), 2H, H-4), 4.11 (s, 2H, H-22), 5.07 (t (6.3 Hz), 1H, H-15), 5.11 (t (6.3 Hz), 1H, H-11), 5.27 (t (7.2 Hz), 1H, H-19), 6.38 (t (3.0 Hz), 1H, H-5), 6.47 (t (3.0 Hz), 1H, H-7), and $^{13}$C NMR (CDCl$_3$, 500 MHz), δ$_C$: 15.8 (C-24), 16.0 (C-23), 16.1 (C-26), 21.3 (C-21), 22.1 (C-10), 22.4 (C-4), 24.1 (C-25), 26.2 (C-18), 26.5 (C-14), 31.3 (C-3), 39.5 (C-17), 39.6 (C-9), 39.8 (C-13), 61.6 (C-22), 75.5 (C-2), 112.6 (C-5), 115.6 (C-7), 121.2 (C-4a), 124.4 (C-11), 124.7 (C-15), 127.3 (C-8), 134.1 (C-20), 134.5 (C-16), 134.9 (C-12), 145.9 (C-8a), 147.7 (C-6) ; HREIMS: m/z 411.2895 [M–H]$^-$ (calcd for C$_{27}$H$_{39}$O$_3$, 411.2905).

γ-Garcinoic acid (compound 32): pale yellow oil; [α]$^{23}_D$-8.5° (c 0.06, MeOH); UV (MeOH) λ$_{max}$ (log ε) 296.0 (3.36), 261.0 (2.88), 206.0 (4.48) nm; $^1$H NMR (CDCl$_3$, 500 MHz), δ$_H$: 1.26 (s, 3H, H-24), 1.54-1.67 (m, 2H, H-9), 1.59 (s, 3H, H-23), 1.59 (s, 3H, H-24), 1.74 (m, 2H, H-3), 1.82 (s, 3H, H-22), 1.97 (m, 2H, H-13), 2.06 (m, 2H, H-14), 2.09 (m, 2H, H-17), 2.11 (s, 3H, H-26), 2.12 (m, 2H, H-10), 2.13 (s, 3H, H-27), 2.28 (m, 2H, H-18), 2.67 (t (6.7 Hz), 2H, H-4), 5.12 (t (7.0 Hz), 1H, H-15), 5.13 (t (7.0 Hz), 1H, H-11), 6.37 (s, 1H, H-5), 6.87 (t (7.4 Hz), 1H, H-19), and $^{13}$C NMR (CDCl$_3$, 500 MHz), δ$_C$: 11.9 (C-26), 11.9 (C-27), 12.1 (C-22), 15.8 (C-24), 15.9 (C-23), 22.1 (C-10), 22.2 (C-4), 24.0 (C-25), 26.4 (C-14), 27.5 (C-18), 31.3 (C-3), 38.0 (C-17), 39.5 (C-13), 39.6 (C-9), 75.2 (C-2), 112.1 (C-5), 118.2 (C-4a), 121.6 (C-7), 124.4 (C-11), 125.1 (C-15), 125.8 (C-8), 126.8 (C-20), 133.7 (C-16), 134.8 (C-12), 144.9 (C-19), 145.6 (C-8a), 146.2 (C-6), 172.6 (C-21) ; HREIMS: m/z 463.2821 [M+Na]$^+$ (calcd for C$_{28}$H$_{40}$O$_4$Na, 463.2819).

Procedures For The Preparation Of
α-Amplexichromanol (Compound 1, Isomer R):

Step 1: Preparation of Compound 4

Compound 4 was prepared according to a procedure described in "Tocopherols by hydride reduction of dialkylamino derivatives", Netscher, Thomas; Mazzini, Francesco; Jestin, Roselyn; Eur. J. Org. Chem. (2007), 1176-1183, DOI: 10.100 2/ oc. 200600874.

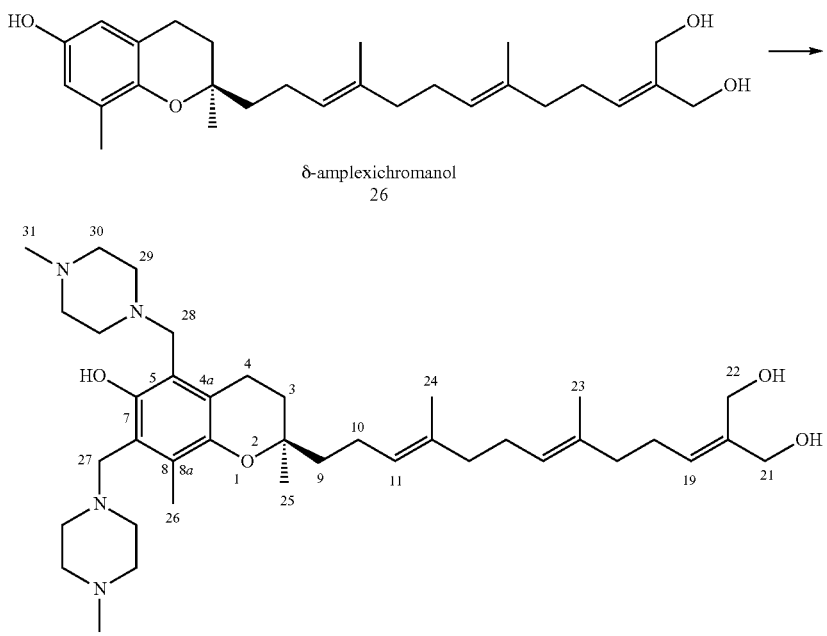

δ-amplexichromanol
26

N-methylpiperazine (1.03 mL, 9.2 mmol, 19 eq) and paraformaldehyde (276 mg, 9.2 mmol, 19 eq) were heated at 70° C. for 2 h and then added to δ-amplexichromanol (200 mg, 0.48 mmol, 1 eq) in MeOH (10 mL). After boiling under refluxed for 48 h, the solvent was evaporated. Methyl tert-butylether (20 mL) and a saturated aqueous solution of Na$_3$PO$_4$ (10 mL) were added to the residue, and the mixture was stirred for 30 min The organic phase was separated, washed with water (3*20 mL), saturated brine (10 mL), dried over Na$_2$SO$_4$ to give, after solvent evaporation under reduced pressure, 290 mg of compound 4 (92% yield).

$^1$H NMR (500 MHz, CD$_3$OD) δ$_H$: 1.24 (s, 3H, H-25), 1.47-1.62 (m, 2H, H-9), 1.52* (s, 3H, H-23), 1.59* (s, 3H, H-24), 1.72-1.83 (m, 2H, H-3), 1.96-1.99 (m, 2H, H-17), 2.00-2.03 (m, 2H, H-13), 2.05-2.07 (m, 2H, H-14), 2.09-2.12 (m, 2H, H-10), 2.13 (s, 3H, H-26), 2.19-2.24 (m, 2H, H-18), 2.29 (s, 6H, H-31, H-31'), 2.35-2.67 (m, 16H, H-29, H-29', H-30, H-30'), 2.74 (t (6 Hz), 2H, H-4), 3.60 (s, 2H, H-28), 3.65 (s, 2H, H-27), 4.08 (s, 2H, H-21), 4.15 (s, 2H, H-22), 5.12 (t (7.2 Hz), 1H, H-15), 5.14 (t (7.2 Hz), 1H, H-11), 5.55 (t (7.2 Hz), 1H, H-19), and $^{13}$C NMR (125 MHz, CD$_3$OD) δ$_C$: 12.0 (C-26), 16.0-16.1 (C-23 and C-24), 21.2 (C-4), 22.3 (C-10), 24.3 (C-25), 27.1 (C-18), 27.6 (C-14), 32.7 (C-3), 40.2 (C-9), 40.3 - 40.5 (C-17 and C-13), 45.9 (C-31, C-31'), 53.0-53.1 (C-29 and C-29'), 54.8 (C-28), 55.5 (C-27), 55.8-55.9 (C-30 and C-30'), 58.3 (C-22), 65.6 (C-21), 75.5 (C-2), 118.5 (C-5), 121.1 (C-7), 121.3 (C-4a), 125.7-125.8 (C-15 and C-11), 126.5 (C-8), 130.7 (C-19), 135.5 - 135.9 (C-16 and C-12), 139.3 (C-20), 145.8 (C-8a), 151.7 (C-6).

FAB-MS: m/z 653.4992 1[M+H]$^+$, (calcd 653.5000 for C$_{39}$H$_{65}$N$_4$O$_4$).

Compound 4 (125 mg, 0.192 mmol, 1 eq) and NaBH$_3$CN (240 mg, 3.84 mmol, 20 eq) in amyl alcohol (2 mL) were irradiated under microwaves at 150° C. for 15 min 10% aqueous HCl (50 mL) was then added, and the mixture was stirred for 3 h. The aqueous phase was extracted with Et$_2$O (3*50 mL), and the combined organic phases washed successively with a saturated aqueous solution of NaHCO$_3$ (50 mL), water (50 mL) and saturated brine (50 mL), dried over Na$_2$SO$_4$ to give after solvent evaporation under reduced pressure 88 mg of crude material. A preparative chromatography (SiO$_2$,) using DCM/MeOH (85:15) yielded a-amplexichromanol (compound 1) (52 mg, 60% yield).

$^1$H NMR (500 MHz, CD$_3$COCD$_3$) δ$_H$: 1.24 (s, 3H, H-25), 1.50-1.64 (m, 2H, H-9), 1.59* (s, 3H, H-23), 1.60* (s, 3H, H-24), 1.74-1.86 (m, 2H, H-3), 1.98-2.01 (m, 4H, H-13, H-17), 2.06-2.09 (m, 2H, H-14), 2.09 (s, 6H, H-26, H-28), 2.13 (s, 3H, H-27), 2.15-2.20 (m, 4H, H-10, H-18), 2.60 (t (6.9 Hz), 2H, H-4), 3.57 (t, (5.6 Hz), 1H, OH-21), 3.65 (t (5.6 Hz), 1H, OH-22), 4.09 (s, 2H, H-21), 4.17 (s, 2H, H-22), 5.11 (t (7.2 Hz), 1H, H-15), 5.16 (t (7.2 Hz), 1H, H-11), 5.47 (t (7.2 Hz), 1H, H-19), 6.48 (s, 1H, OH), and $^{13}$C NMR (125 MHz, CD$_3$COCD$_3$) δ$_C$: 10.8 (C-28), 11.0 (C-30), 11.7 (C-26), 15.9-16.0 (C-23 and C-24), 20.3 (C-4), 21.9 (C-10), 23.1 (C-25), 25.6 (C-18), 26.2 (C-14), 31.4 (C-3), 38.9 (C-9), 39.3 (C-17), 39.4 (C-13), 57.9 (C-22), 64.9 (C-21), 73.7 (C-2), 116.8 (C-4a), 119.5 (C-5), 121.4 (C-8), 122.0 (C-7), 124.2-124.5 (C-11 and C-15), 126.7 (C-19), 134.3 (C-16), 134.3 (C-12), 139.1 (C-20), 144.9 (C-8a), 145.3 (C-6).

HRESIMS: m/z 479.3126 [M+Na]$^+$, (calcd for C$_{29}$H$_{44}$O$_4$Na, 479.3132).

Step 2: Preparation of α-amplexichromanol
(Compound 1, Isomer R)

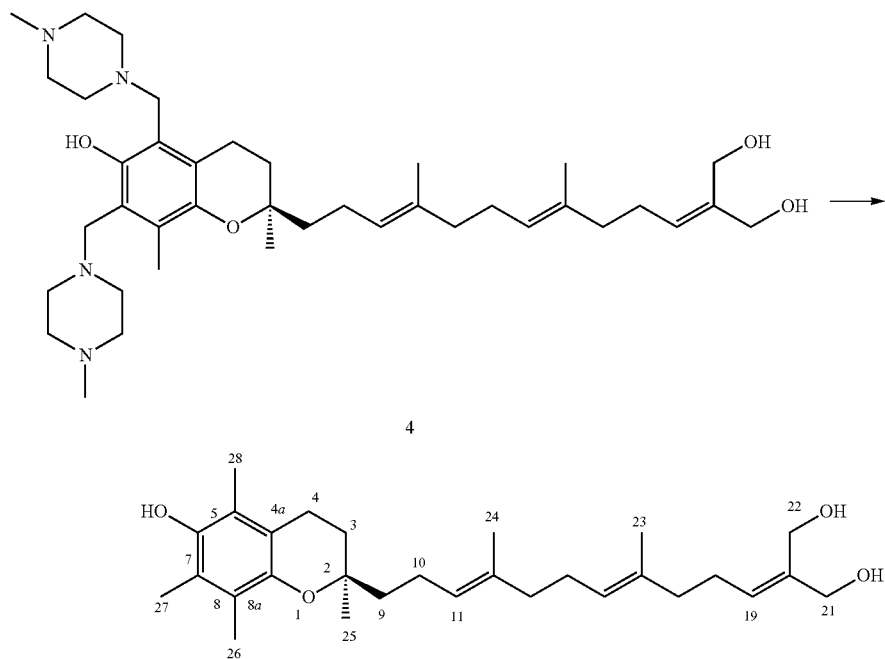

Procedures for the Preparation of
β-amplexichromanol (Compound 9, Isomer R):

Step 1: Preparation of Compound 15

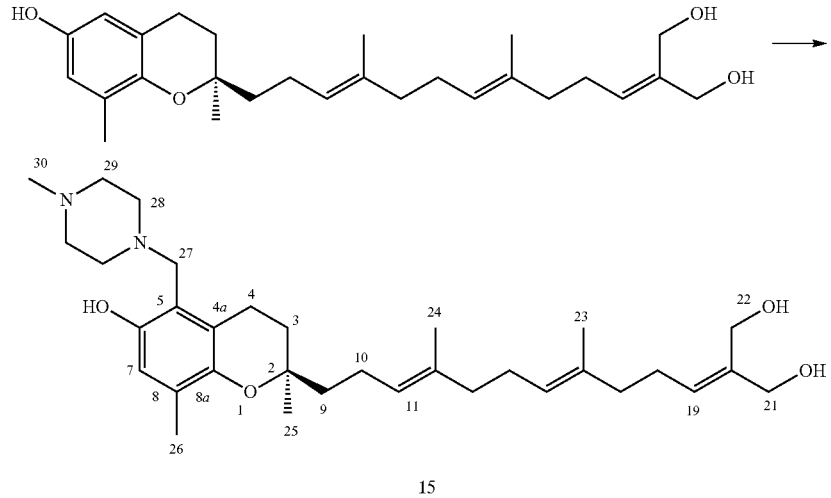

15

The same procedure as described for compound 4 using N-methylpiperazine (192 mg, 1.68 mmol, 3 eq), paraformaldehyde (51 mg, 1.68 mmol, 3 eq) and δ-amplexichromanol (236 mg, 0.56 mmole, 1 eq) was carried out to yield compound 15 (280 mg, 92%).

$^1$H NMR (500 MHz, CD$_3$COCD$_3$) $\delta_H$: 1.23 (s, 3H, H-25), 1.49-1.63 (m, 2H, H-9), 1.59 (s, 6H, H-23, H-24), 1.71-1.85 (m, 2H, H-3), 1.96-2.01 (m, 2H, H-13), 1.96-2.01 (m, 2H, H-17), 2.06-2.09 (m, 2H, H-14), 2.07 (s, 3H, H-26), 2.11-2.20 (m, 2H, H-10), 2.11-2.20 (m, 2H, H-18), 2.22 (s, 3H, H-30), 2.65 (t (6.9 Hz), 2H, H-4), 3.63 (s, 2H, H-27), 4.10 (s, 2H, H-21), 4.17 (s, 2H, H-22), 5.12 (t (7.2 Hz), 1H, H-15), 5.15 (t (7.2 Hz), 1H, H-11), 5.47 (t (7.2 Hz), 1H, H-19), 6.39 (s, 1H, H-7), and $^{13}$C NMR (125 MHz, CD$_3$COCD$_3$) $\delta_C$: 15.9 (C-24), 16.1 (C-26), 16.3 (C-23), 21.1 (C-4), 22.8 (C-10), 24.1 (C-25), 26.7 (C-18), 27.2 (C-14), 32.3 (C-3), 39.7 (C-9), 40.3 (C-17), 40.5 (C-13), 46.1 (C-30), 53.1 (C-28, C-28'), 55.8 (C-29, C-29'), 56.7 (C-27), 58.9 (C-22), 65.9 (C-21), 74.7 (C-2), 117.0 (C-5, C-7), 119.8 (C-4a), 125.2 (C-15), 125.5 (C-11), 126.4 (C-8), 127.6 (C-19), 135.3-135.4 (C-12 and C-16), 140.2 (C-20), 145.2 (C-8a), 151.5 (C-6).

FAB-MS m/z 541.3992 [M+H]$^+$, (calcd for C$_{33}$H$_{53}$N$_2$O$_4$, 541.3999).

Step 2: Preparation of Compound
β-amplexichromanol (Compound 9)

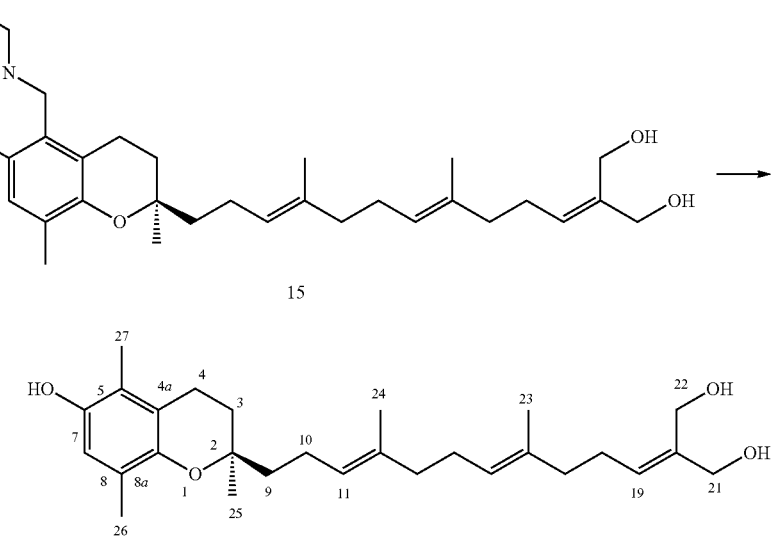

9

The same procedure as described for compound 1, using compound 15 (200 mg, 0.37 mmol, 1 eq) and NaBH$_3$CN (232 mg, 3.7 mmol, 10 eq), was carried out in amyl alcohol (2 mL) to yield δ-amplexichromanol (compound 9, 115 mg, 71%).

$^1$H NMR (500 MHz, CD$_3$COCD$_3$) δ$_H$: 1.24 (s, 3H, H-25), 1.50-1.64 (m, 2H, H-9), 1.59* (s, 6H, H-23), 1.60* (s, 3H, H-24), 1.74-1.86 (m, 2H, H-3), 1.96-2.01 (m, 2H, H-13), 1.96-2.01 (m, 2H, H-17), 2.04 (s, 3H, H-27), 2.05 (s, 3H, H-26), 2.09 (m, 2H, H-14), 2.12-2.20 (m, 2H, H-10), 2.12-2.20 (m, 2H, H-18), 2.60 (t (6.9 Hz), 2H, H-4), 3.62 (t (5.6 Hz), 1H, OH-21), 3.70 (t (5.6 Hz), 1H, OH-22), 4.10 (s, 2H, H-21), 4.18 (s, 2H, H-22), 5.13 (t (7.2 Hz), 1H, H-15), 5.16 (t (7.2 Hz), 1H, H-11), 5.47 (t (7.2 Hz), 1H, H-19), 6.51 (s, 1H, H-7), 7.38 (s, 1H, OH), and $^{13}$C NMR (125 MHz, CD$_3$COCD$_3$) δ$_C$: 11.2 (C-26), 15.9 (C-27), 16.1 (C-23, C-24), 21.3 (C-4), 22.9 (C-10), 24.2 (C-25), 26.6 (C-18), 27.2 (C-14), 32.3 (C-3), 39.8 (C-9), 40.3 (C-17), 40.4 (C-13), 58.5 (C-22), 65.9 (C-21), 74.6 (C-2), 123.7 (C-8), 115.9 (C-7), 120.2 (C-5), 121.0 (C-4a), 125.2 (C-15), 125.5 (C-11), 127.8 (C-19), 135.2-135.3 (C-12 and C-16), 140.1 (C-20), 145.7 (C-8a), 148.1 (C-6).

FAB-MS m/z 442.3095 [M]$^+$, (calcd for C$_{28}$H$_{42}$O$_4$, 442.3078).

BIOLOGY EXAMPLES

Example 1

Binding of Human 5-lipoxygenase (5-LO) to δ-garcinoic Acid (Compound 27—Reference Compound)

The aim of this experiment is to show that 5-LO has a good binding affinity for δ-garcinoic acid (GA).

In this purpose, two groups were formed:
the control (ctrl) which consists of pearls on which phenoxybutyric acid is immobilized at the surface; and
the sample (GA-Toyo) which consists of pearls on which δ-garcinoic acid is immobilized at the surface (Toyopearl® AF Amino 650).

Then, a solution comprising human semi-purified 5-LO is added on each group of pearls.

Human 5-LO was expressed in *E. coli* and semi-purified by ATP affinity chromatography as previously described (Koeberle, Biochem. Pharmacol. 2009 May 1; 77 (9): 1513-21).

δ-garcinoic acid (30 mg) or phenoxybutyric acid (12,3 mg) were dissolved in methanol/H$_2$O (98/2) pH 4-6. Washed Toyopearl AF Amino 650 resin (500 µl) and 1-ethyl-3-(3-dimethylaminopropyl)carbodiimide (EDC, 40 mg) were added, and the mixture incubated for 48 h at room temperature. The pH was regularly controlled and readjusted to pH 5. Resins with immobilized δ-garcinoic acid (GA-Toxo) and phenoxybutyric acid (ctrl) were washed and stored in methanol/water (20/80) at 4° C.

To investigate the binding of 5-LO to GA-Toyo and the control, the washed and drained resins were added to binding buffer (50 mM HEPES, pH 7.4, 200 mM NaCl, 1 mM EDTA; 500 µl) containing 100 µg milk powder and 0.01% triton X-100 and incubated for 1 h at 4° C. under rotation. Then, human semi-purified 5-LO was added (approx. 5 µg) and incubation continued for 1 h. After intensive washing of the resins with binding buffer, bound proteins were dissolved in Lammli buffer (50 µl, 2×) by heating to 96° C. for 5 min. Proteins were separated by SDS-polyacrylamide gel electrophoreses (SDS-PAGE), and 5-LO was detected by Western Blot as previously described (Pergola: Proc Natl Acad Sci U S A. 2008 Dec 16; 105 (50): 19881-6.), Blots were densitometrically analyzed and are background-corrected.

Figure 2:
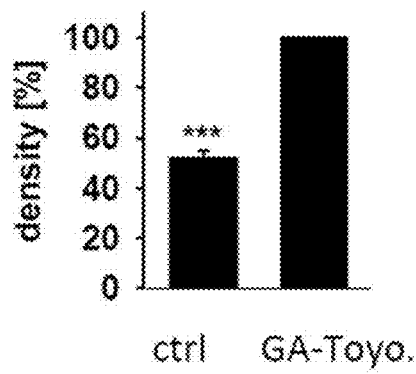
FIG. 2 is a graph showing the binding of 5-LO to δ-garcinoic acid-immobilized Toyopearls®.

The results are presented in FIG. 2 and show that the binding of 5-LO to GA-Toyo pearls is twofold higher than with the control.

Thus, this result evidences that δ-garcinoic acid directly binds to the enzyme 5-LO.

Example 2

Binding Site for δ-garcinoic Acid (Compound 27—Reference Compound) on 5-LO

In a first approach, the 5-LO product formation was measured in function of the concentration of garcinoic acid (0; 0.01; 0.03; 0.1; 0.3 or 1 µM) on human recombinant 5-LO in presence of various concentration of arachidonic acid (5; 20; 40 or 80 µM).

In the case of no garcinoic acid in the medium, the 5-LO product formation is considered as being 100% (reference).

Figure 3A:
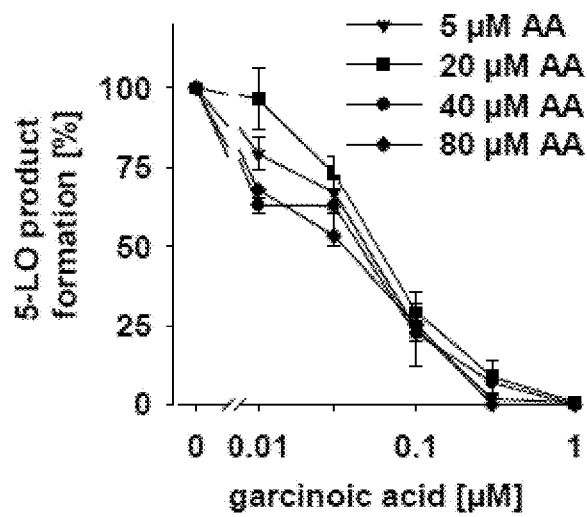
FIG. 3A is a graph showing 5-LO product formation (%) by semi-purified human 5-LO in function of δ-garcinoic acid concentration upon treatment with different concentrations of arachidonic acid (AA).

The results (FIG. 3A) show that:
at a concentration lower than 1 µM of garcinoic acid in the medium, the 5-LO product formation is partially inhibited;
at 1 µM of garcinoic acid in the medium, the 5-LO product formation is totally inhibited;
the presence of various concentrations of arachidonic acid in the medium does not influence the inhibition of 5-LO product formation by garcinoic acid.

In a second approach, the binding between garcinoic acid and 5-LO in presence of arachidonic acid, was studied. The aim is to evaluate the competition between garcinoic acid and the conventional substrate of the enzyme.

For this purpose, garcinoic acid immobilized on Toyopearls® (GA-TOYO) was used and the density of the 5-LO binding to GA-TOYO was measured. This experiment was realized in absence (w/o) or in presence of arachidonic acid at a concentration of 100 µM.

Figure 3B:
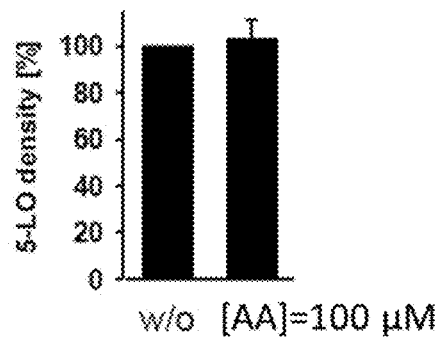
FIG. 3B is a graph showing the binding of 5-LO to δ-garcinoic acid-immobilized pearls in presence of arachidonic acid solution (100 μM) or vehicle (w/o).

The results are presented in FIG. 3B.

In the absence of AA (i.e. w/o column), the 5-LO density obtained by the binding of 5-LO to immobilized garcinoic acid, is considered as being 100% (reference).

In presence of AA (100 µM), the 5-LO density was expected to be lower than 100% if AA competes with garcinoic acid.

The binding of 5-LO is not affected by the AA concentration in the buffer.

Thus, these results highlight that garcinoic acid does not compete with arachidonic acid for binding 5-LO. These results show that garcinoic acid is a non-competitive inhibitor of 5-LO.

Example 3

Effect of δ-amplexichromanol (Compound 26) on the Formation of Proinflammatory Mediators Chronic airway disorders are associated with chronic inflammatory diseases. Thus, there is a need to develop alternative treatments allowing decreasing of the formation of proinflammatory mediators.

The aim of this experiment is to show that tocotrienol derivatives of the invention decrease the formation of proinflammatory mediators such as IL-1β, TNF-α and IL-8.

Figure 4:
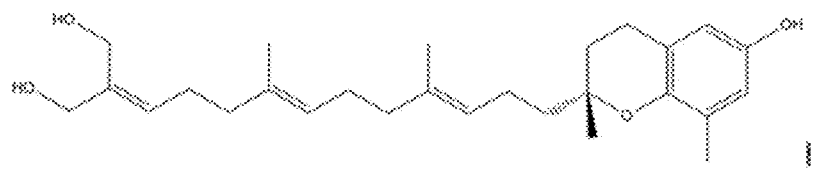
FIG. 4 is a scheme of the structure of δ-amplexichromanol (compound 26).

In this study, the tocotrienol derivative is δ-amplexichromanol (compound 26). Its structure is presented in FIG. 4.

First, different concentrations of δ-amplexichromanol (0.1; 1 and 10 μM) were added to the stimulated monocytes.

Secondly, monocytes were stimulated with lipopolysaccharide (LPS, 10 ng/ml for 4-18 h) for inducing the formation of pro-inflammatory cytokines.

Finally, the resulting levels of proinflammatory cytokines were measured by ELISA. Dexamethasone (1 μM) was used as control.

The results are presented on Tables 2 and 3.

TABLE 2

| Compound | Concentration (μM) | IL-1β release (%) | TNF-α release (%) | IL-8 release (%) |
|---|---|---|---|---|
| δ-amplexichromanol | 1 | 86 ± 11 | n.i.[a] | n.i.[a] |
| | 10 | 49.9 ± 4.8 | 13.3 ± 2.6 | 30.6 ± 1.5 |
| dexamethasone | 1 | 68.7 ± 2.4 | 42.2 ± 0.8 | 83.5 ± 3.2 |

[a] no inhibition.

TABLE 3

| Compound | Concentration (μM) | 5-LO product formation in neutrophils (AA + A23187) residual activities [% vehicle control] | 5-LO product formation in neutrophils (A23187) residual activities [% vehicle control] | human recombinant 5-LO residual activities [% vehicle control] |
|---|---|---|---|---|
| δ-amplexichromanol | 0.1 | n.i.[a] | 17.4 ± 8.8 | 43.0 ± 13.3 |
| | 1 | 15.4 ± 4.4 | 10.0 ± 2.8 | 1.5 ± 0.7 |
| | 10 | 0.6 ± 0.6 | 0.0 ± 0.0 | 0.1 ± 0.1 |

Freshly isolated neutrophils (1×10⁷/ml) were pre-incubated with the test compounds for 15 min at 37° C. Then, 5-LO product formation was started by addition of 2.5 μM $Ca^{2+}$-ionophore A23187 alone or A23187 plus 20 μM arachidonic acid (AA). The reaction was stopped after 10 min at 37° C. with 1 ml of methanol. Major 5-LO metabolites ($LTB_4$ and its all-trans isomers and 5-H(P)ETE) were extracted and analyzed by HPLC as described (Werz: Blood 2002, 99, 1044-1052). Cysteinyl-LTs $C_4$, $D_4$ and $E_4$ and oxidation products of $LTB_4$ were not determined.

Human recombinant 5-LO was pre-incubated with the test compounds for 10 min at 4° C. and pre-warmed for 30 s at 37° C. 5-LO product formation was initiated by addition of 2 mM $CaCl_2$ and 20 μM arachidonic acid. After 10 min at 37° C., the reaction was terminated by addition of 1 ml ice-cold methanol. Formed 5-LO metabolites (all-trans isomers of LTB4 and 5-H(P)ETE) were analyzed by RP-HPLC as described (Koeberle: Biochem. Pharmacol. 2009, 77, 1513-1521).

Results

The results of Table 2 show that δ-amplexichromanol at 10 μM decreases the release of pro-inflammatory cytokines being more efficient than the control dexamethasone.

The results of Table 3 confirm δ-amplexichromanol as potent inhibitor of human recombinant 5-LO and 5-LO product formation in neutrophils.

Example 4

Effect of α-amplexichromanol and Tocotrienol Derivatives on Human Recombinant 5-LO Activity and Neutrophil 5-LO Product Formation The aim of this study is to show the ability of compounds of the invention for selective and non-competitive inhibition of 5-lipoxygenase (5-LO) and for inhibition of the neutrophil 5-LO product formation.

BWA4C is a selective inhibitor of 5-LO and inhibits the synthesis of leukotriene $B_4$ ($LTB_4$) involved in inflammation. In these experiments, BWA4C is used as positive control compound.

δ-garcinoic acid is used as a reference compound.
Biological results are presented in Table 4.

TABLE 4

| | | $IC_{50}$ (nM) | |
|---|---|---|---|
| Ref. | Cpd. | 5-LO activity | neutrophil 5-LO product formation |
| BWA4C (control) | | 26 ± 6 | 41 ± 1 |
| δ-TE-(E)-13'-COOH (δ-garcinoic acid) Reference compound | 27 | 57 ± 9 | 345 ± 73 |
| α-TE-13'- diOH α-amplexichromanol | 1 | 106 ± 29 | 19 ± 4 |
| β-TE-13'- diOH | 9 | 91 ± 15 | 114 ± 35 |
| γ-TE-(Z)-13'-OH (γ-deoxyamplexichromanol) | 33 | 120 ± 29 | 140 ± 21 |
| γ-TE-13'- diOH (γ-amplexichromanol) | 34 | 110 ± 0 | 67 ± 54 |
| δ-TE-(Z)-13'-OH (δ-(Z)-deoxyamplexichromanol) | 23 | 137 ± 29 | 220 ± 40 |
| δ-TE-13'-diOH (δ-amplexichromanol) | 26 | 148 ± 35 | 419 ± 33 |

These results show that the tocotrienol derivatives of the invention are more potent inhibitors of neutrophil 5-LO product formation compared to δ-garcinoic acid. Furthermore, the compounds of the invention feature an efficient inhibition of the human recombinant 5-LO.

Example 5

Effect of α-amplexichromanol (Compound 1) on $LTC_4$ Formation Compared to ZYFLO®

The aim is to show the efficiency of tocotrienol derivatives having a ω-oxidized side chain on the reduction of leukotrienes $C_4$ ($LTC_4$) in comparison with the commercial product Zileuton (ZYFLO®). In this study, the tocotrienol derivative is α-amplexichromanol (compound 1).

Zymosan was used to trigger peritonitis in mice pretreated with a-amplexichromanol or Zileuton, each at a dose of 10 mg/kg. The resulting $LTC_4$ levels in the peritoneal exudate were measured 30 min after zymosan injection.

Detailed Protocol

α-amplexichromanol (10 mg/kg) or vehicle (0.5 ml of 0.9% saline solution containing 2% DMSO) were given i.p. 30 min before zymosan i.p. injection (0.5 ml of a 2 mg/ml suspension in 0.9% w/v saline). Mice were killed by inhalation of $CO_2$ at the indicated time points followed by a peritoneal lavage with 3 ml of cold PBS pH 7.4. Exudates were collected. After centrifugation of the exudates (18,000× g, 5 min, 4° C.), the amounts of cysteinyl-LTs were analyzed in the supernatant by enzyme immunoassay (Enzo Life Sciences GmbH, Lörrach, Germany) according to manufacturer's instructions.

Figure 5:
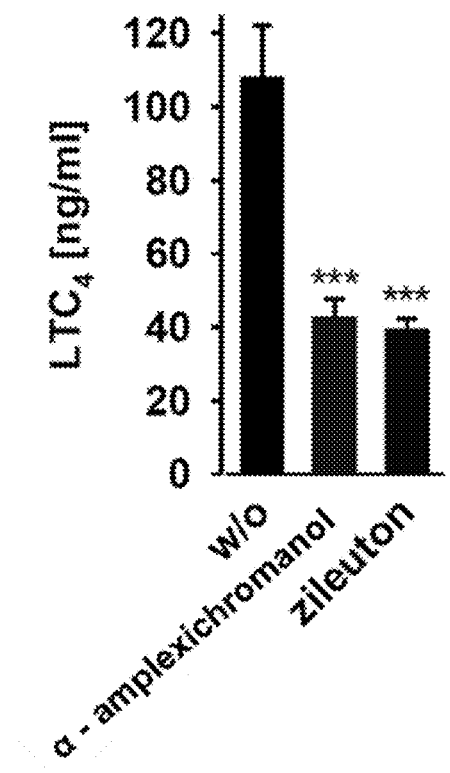
FIG. 5 is a graph showing the LTC$_4$ level (ng/ml) in mice after intraperitoneal (i.p.) administration of vehicle, α-amplexichromanolor Zileuton and subsequent induction of peritonitis by i.p. injection of zymosan.

The results (FIG. 5) show that $LTC_4$ level resulting from the treatment based on α-amplexichromanol is the same than the $LTC_4$ level obtained by Zileuton.

Thus, tocotrienol derivatives having an ω-oxidized side chain allow achieving the same efficiency on reduction of $LTC_4$ as currently available drugs for asthma. These results suggest that toctorienol derivatives might be a good alternative to currently available drugs.

Example 6

Hepatotoxicity Assay

The aim is to evaluate the potential toxicity induced by the tocotrienol derivatives of the invention on the liver.

Protocol

HepaRG® cells were seeded at a density of $2.6 \times 10^4$ cells/cm² in Williams' E medium supplemented with 2 mM glutamax, 100 U/mL penicillin, 100 µg/mL streptomycin, 10% Hyclone fetal calf serum, 5 µg/mL insulin, and 50 mM hydrocortisone hemisuccinate. At confluence, after 2 weeks, HepaRG® cells were shifted to the same medium supplemented with 1.7% dimethyl sulfoxide for 2 additional weeks in order to obtain confluent differentiated cultures containing equal proportions of hepatocyte-like and progenitors/primitive biliary-like cell. These differentiated hepatic cell cultures were used for analytical assays.

Then, the cells were exposed to a tocotrienol derivative in Williams' E medium supplemented with 2% Hyclone fetal calf serum containing 0.2% dimethyl sulfoxide during 48 h.

Four tocotrienol derivatives were studied:
1. α-amplexichromanol (compound 1);
2. β-amplexichromanol (compound 9);
3. γ-amplexichromanol (compound 34);
4. deoxyamplexichromanol (compound 33).

Amplexichromanol are tocotrienol derivatives having a w-oxidized side chain with a diol. Deoxyamplexichromanol is a tocotrienol derivative having a w-oxidized side chain with only one alcohol function.

A comparison was done with Zileuton (ZYFLO®). The results are presented Table 5.

TABLE 5

| Concentration (µM) | DMSO | Number of cells | | |
| --- | --- | --- | --- | --- |
| | | 0.1 | 1 | 10 |
| α-amplexichromanol | 4074 | 4389 | 4705 | 4702 |
| β-amplexichromanol | 4292 | 4429 | 4436 | 4785 |
| γ-amplexichromanol | 4158 | 4212 | 4562 | 4677 |
| deoxyamplexichromanol. | — | 4363 | 4412 | 4610 |
| Zileuton | 4458 | 4313 | 4244 | 4554 |

The results show that for a concentration about 0.1, 1 or 10 µM, the number of liver cells are maintained for each tocotrienol derivative and are similar of the results obtained from Zileuton.

Thus, this study evidences that the tocotrienol derivatives do not induce any toxicity on the liver.

The invention claimed is:

1. A tocotrienol derivative of general formula (IV)

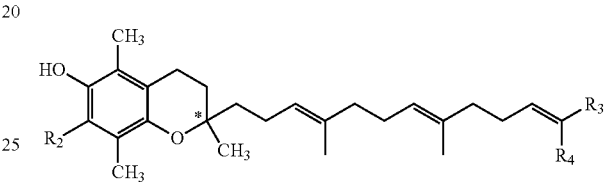

and pharmaceutically acceptable salts and/or solvates thereof, wherein:
* stands for the (R)-enantiomer, the (S)-enantiomer, for the racemate or for the non-racemic mixture of (R) and (S) enantiomers of the corresponding formula (IV);
$R_2$ is H or alkyl; $R_3$ and $R_4$ are identical or different and each one is selected from the group of amido, alkyl, carboxyl, hydroxyl and formyl; and
wherein at least one of $R_3$ or $R_4$ is an alkyl substituted by at least one group selected from hydroxyl, carboxyl or formyl.

2. The tocotrienol derivative according to claim 1, wherein the tocotrienol derivative is the (R)-enantiomer.

3. The tocotrienol derivative according to claim 1, wherein $R_2$ is $CH_3$.

4. The tocotrienol derivative according to claim 1, wherein $R_3$ and $R_4$ are selected such that the stereochemistry of double bond C═C to which they are attached is (E).

5. The tocotrienol derivative according to claim 1 selected from:

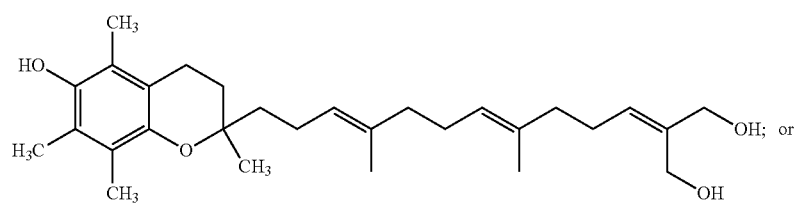

compound 1

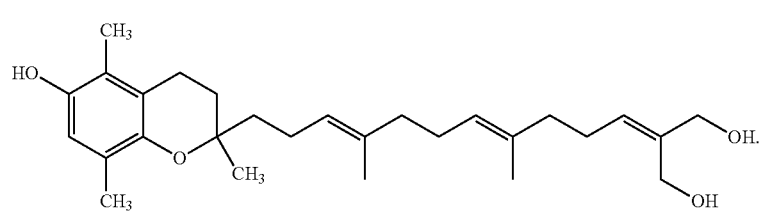

compound 9

6. A pharmaceutical composition comprising at least one tocotrienol derivative according to claim 1, and at least one pharmaceutically acceptable carrier, diluent, excipient and/or adjuvant.

7. A medicament comprising at least one tocotrienol derivative according to claim 1, or pharmaceutically acceptable salts and/or solvates thereof.

8. The tocotrienol derivative of claim 1, wherein alkyl is substituted by at least one group selected from hydroxyl, carboxyl, oxo, amido, amino and formyl.

9. The tocotrienol derivative of claim 1, wherein amido group is substituted by at least one group selected from alkyl, arylalkyl or alkylaryl.

10. The tocotrienol derivative of claim 8, wherein amido group is substituted by at least one group selected from alkyl, arylalkyl or alkylaryl.

11. The tocotrienol derivative according to claim 9, wherein the tocotrienol derivative is the (R)-enantiomer.

\* \* \* \* \*